United States Patent
Hanes et al.

(10) Patent No.: US 10,695,442 B2
(45) Date of Patent: Jun. 30, 2020

(54) ENGINEERING SYNTHETIC BRAIN PENETRATING GENE VECTORS

(71) Applicant: The Johns Hopkins University, Baltimore, MD (US)

(72) Inventors: Justin Hanes, Baltimore, MD (US); Jung Soo Suk, Baltimore, MD (US); Panagiotis Mastorakos, Charlottesville, VA (US); Graeme Woodworth, Baltimore, MD (US); Clark Zhang, Sunnyvale, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/914,796

(22) Filed: Mar. 7, 2018

(65) Prior Publication Data

US 2018/0193488 A1    Jul. 12, 2018

Related U.S. Application Data

(63) Continuation of application No. 15/310,535, filed as application No. PCT/US2015/030381 on May 12, 2015, now Pat. No. 9,937,270.

(60) Provisional application No. 61/991,898, filed on May 12, 2014, provisional application No. 61/991,920, filed on May 12, 2014, provisional application No. 62/001,994, filed on May 22, 2014.

(51) Int. Cl.
| | |
|---|---|
| *A61K 9/00* | (2006.01) |
| *A61K 9/51* | (2006.01) |
| *A61K 47/60* | (2017.01) |
| *A61K 47/69* | (2017.01) |
| *A61K 48/00* | (2006.01) |
| *C12N 15/88* | (2006.01) |

(52) U.S. Cl.
CPC ........ *A61K 48/0008* (2013.01); *A61K 9/0085* (2013.01); *A61K 9/51* (2013.01); *A61K 9/5146* (2013.01); *A61K 9/5169* (2013.01); *A61K 9/5192* (2013.01); *A61K 47/60* (2017.08); *A61K 47/6935* (2017.08); *A61K 48/0075* (2013.01); *C12N 15/88* (2013.01)

(58) Field of Classification Search
CPC .......... A61L 27/26; A61L 27/50; A61L 27/52; A61L 27/54; A61L 2300/434; A61L 2400/06; A61L 2430/24; A61K 47/38; A61K 31/155; A61K 9/0024; A61K 9/06; A61K 47/34; A61K 31/515; A61K 47/36; A61K 48/0008; A61K 47/6935; A61K 47/60; A61K 9/5192; A61K 9/5169; A61K 48/0075; A61K 9/51; A61K 9/5146; A61K 9/0085; A61P 19/02; C12N 15/88

See application file for complete search history.

(56) References Cited

U.S. PATENT DOCUMENTS

| | | |
|---|---|---|
| 5,034,506 A | 7/1991 | Summerton |
| 5,527,675 A | 6/1996 | Coull |
| 5,539,082 A | 7/1996 | Nielsen |
| 5,623,049 A | 4/1997 | L obberding |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 2006/0223777 A1 | 10/2006 | Vermeulen |
| 2007/0213292 A1 | 9/2007 | Stoffel |
| 2007/0219122 A1 | 9/2007 | Glazer |
| 2008/0050920 A1 | 2/2008 | Kawahara |
| 2011/0262406 A1 | 10/2011 | Campo |
| 2012/0310140 A1* | 12/2012 | Kramer ................ A61K 9/0009 604/20 |
| 2013/0211380 A1* | 8/2013 | Cabrera Aquino ... A61M 5/178 604/508 |

FOREIGN PATENT DOCUMENTS

| | | |
|---|---|---|
| WO | 0180832 | 11/2001 |
| WO | 0203848 | 1/2002 |
| WO | 2005013901 | 2/2005 |

(Continued)

OTHER PUBLICATIONS

Nance et al. ("A Dense Poly(ethylene glycol) Coating Improves Penetration of Large Polymeric Nanoparticles within Brain Tissue", 2012) (Year: 2012).*

Farrell et al. "A comparison of the effectiveness of cationic polymers poly-l-lysine (PLL) and polyethylenimine (PEI) for non-viral delivery of plasmid DNA to bone marrow stromal cells (BMSC)", European Journal of Pharmaceutics and Biopharmaceutics, Mar. 2007, p. 388-397. (Year: 2007).*

Bergstrand et al. "Comparison of PEI-PEG and PLL-PEG copolymer coatings on the prevention of protein fouling", Journal of Biomedical Materials Research, Mar. 3, 2008, p. 608-615. (Year: 2008).*

(Continued)

*Primary Examiner* — Robert A Wax
*Assistant Examiner* — Quanglong N Truong
(74) *Attorney, Agent, or Firm* — Pabst Patent Group LLP

(57) ABSTRACT

A synthetic gene delivery platform with a dense surface coating of hydrophilic and neutrally charged PEG, capable of rapid diffusion and widespread distribution in brain tissue, and highly effective gene delivery to target cells therein has been developed. Nanoparticles including nucleic acids, are formed of a blend of biocompatible hydrophilic cationic polymers and they hydrophilic cationic polymer conjugated to hydrophilic neutrally charged polymers such as polyethylene glycol. The nanoparticles are coated with polyethylene glycol at a density that imparts a near neutral charge and optimizes rapid diffusion through the brain parenchyma. Methods of treating a disease or disorder of the brain including administering a therapeutically effective amount of nanoparticles densely coated with polyethylene glycol are also provided.

20 Claims, 19 Drawing Sheets

(56) References Cited

FOREIGN PATENT DOCUMENTS

| WO | WO2002044321 | 2/2005 | | |
|---|---|---|---|---|
| WO | 2005023986 | 3/2005 | | |
| WO | 2006112872 | 10/2006 | | |
| WO | 2006093526 | 12/2006 | | |
| WO | 2007021896 | 2/2007 | | |
| WO | 2007027775 | 3/2007 | | |
| WO | 2007027894 | 3/2007 | | |
| WO | 2007090073 | 8/2007 | | |
| WO | 2007112754 | 10/2007 | | |
| WO | 2008046911 | 4/2008 | | |
| WO | 2008074328 | 6/2008 | | |
| WO | 2008091703 | 7/2008 | | |
| WO | 2009020771 | 2/2009 | | |
| WO | 2007112753 | 7/2009 | | |
| WO | 2012039979 | 3/2012 | | |
| WO | WO 2012109363 A2 | 8/2012 | ........ | A61K 47/48192 |
| WO | WO-2012109363 A2 * | 8/2012 | ............ | C12N 15/87 |

OTHER PUBLICATIONS

Bernstein, et al., "Role for a bidentate ribonuclease in the initiation step of RVA interference", Nature, 409:363-6 (2001).

Boussif, et al., "A versatile vector for gene and oligonucleotide transfer into cells in culture and in vivo: polyethylenimine", PNAS, 92(16):7297-301 (1995).

Demeneix and Behr, "Polyethylenimine (PEI)", Adv Genet., 53PA:215-30 (2005).

Elbashir, et al., "RNA interference is mediated y 21-and 22-nucleotide RNAs", Gene Dev., 15:188-200 (2001a).

Elbashir, et al., "Duplexes of 21±nucleotide RNAs mediate RNA interference in cultured mammalian cells", Nature, 411:494-8 (2001b).

Eliott, et al., "EB1 is essential during *Drosophila* development and plays a crucial role in the integrity of chordotonal mechanosensory organs", Mal Biol Cell, 16(2):891-901 (2005).

Ferrari, et al., "Polyethylenimine shows properties of interest for cystic fibrosis gene therapy", Biochim Biophys Acta., 1447(2-3):219-25 (1999).

Fire, et al., "Potent and specific genetic interference by double-strandedRNAin caenorhabditis elegans", Nature, 391:806-11 (1998).

Griffith-Jones, et al., "miRBase tools for microRNA genomics", Nucleic Acids Res., 36(darabase issue):D140-4 (2008).

Hammond, et al., "An RNA-directed nuclease mediates post-transcriptional gene silencing in *Drosophila* cells", Nature, 404:293-6 (2000).

Hannon, et al., "RNA interference", Nature, 418:244-51 (2002).

Hosmane, et al., "Toll/interleukin-1 receptor domain-containing adapter inducing interferon-B mediates microglial phagocytosis of degenerating axons", J Neursci., 32(22):7745-57 (2012).

Hu, et al., "reaction parameters of targeted gene repair in mammalian cells", Mol Biotech., 29:197-210 (2005).

Konstan, et al., "Compacted DNA nanoparticles administered to the nasal mucosa of cystic fibrosis subjects are safe and demonstrate partial to complete cystic fibrosis transmembrane regulator reconstitution", Hum Gene Ther., 15(12):1255-69 (2004).

Kroll, et al., "Outwitting the blood-brain barrier for therapeutic purposes: osmotic opening and other means", Neurosurgery, 42(5):1083-99 (1998).

Kukowska-Latallo, et al., "Intravascular and endobronchial DNA delivery to murine lung tissue using a novel nonviral vector", Hum Gene Ther., 11(10):1385-95 (2000).

Liang, et al., "Delivery of cationic polymer-siRNA nanoparticles for gene therapies in neural regeneration", Biochem Biophys Res Comm., 421(4):690-5 (2012).

Liu, et al., "Strain-based genetic differences regulate the efficiency of systemic gene delivery as well as expression", J Biol Chem., 277(7):4966-72 (2002).

Martin, et al., "Apparent subdiffusion inherent to single particle tracking", Biophys J, 83(4):2109-17 (2002).

Martinez, et al.,., "Single-stranded antisense siRNAs guide target RNA cleavage in RNA", Cell, 110:563-74 (2002).

Napoli, et al., "Introduction of a chimeric chalcone synthase gene into petunia results in reversible co-suppression of homologous genes in trans", Plant Cell, 2:279-89 (1990).

Neu, et al., "recent advances in national gene transfer vector design based on poly (ethyleneimine) and its derivatives", J Gne Med., 7(8):992-1009 (2005).

Ogris, et al., "DNA/polyethylenimine transfection particles influence of ligands polymer size and PEGylation on internalization and gene expression", AAPS Pharm Sci., 3(3):891-901 (2005).

Olsen, et al., "Genomic sequence correction by single-stranded DNA oligonucleotides role of DNA synthesis and chemical modifications of the oligonucleotide ends", J Gene Med., 7:1534-44 (2005).

Padmapriya, et al., "Synthesis of oligodeoxynucleoside methylphonothioates", Bioorg Med Chem Lett., 3:761 (1993).

Patel, et al., "Polymeric nanoparticles for drug delivery to the central nervous system", Adv Drug Deliv Rev., 64(7):701-5 (2012).

Recoinos, et al., "Combination of intracranial temozolornide with intracranial carmustine improves survival when compared with either treatment alone in a rodent glioma model", Neurosurgery, 68(3):530-7 (2010).

Savan, et al., "Static and dynamic errors in particle tracing microrheology", Biophys J, 88(1):623-38 (2005).

Schubert, et al., "Gene delivery to the nervous system", Mol Ther., 16(4):640-6 (2008).

Schuster, et al., "Nanoparticle diffusion in respiratory mucus from humans without lung disease", Biomaterials, 34(13):3439-46 (2013).

Sonawane, et al., "Chloride accumulation and swelling in endosomes enhances DNA transfer by polyamine-DNA polyplexes", J Biol Chem., 278(45):44826-31 (2003).

Suk, et al., "Gene delivery to differentiated neurotypic cells with RGD and HIC Tat peptide functionalized polymeric nanoparticles", Biomaterials, 27:5143-50 (2006).

Uhlmann, et al., "Antisense oligonucleotides: A new therapeutic principle", Chem Rev., 90:544-79 (1990).

Ui-Tei, et al., "Sensitive assay of RNA interference in *Drosophila* and Chinese hamster cultured cells using firefly luciferase gene as target", FEBS Lett., 479:79-82 (2000).

Vykhodtseva, et al., "Progress and problems in the application of focused ultrasound for blood-brain barrier disruption", Ultrasonics, 48(4):279-96 (2008).

Zamecnik, "The extracellular space and matrix of gliomas", Acta Neuropathol., 110(5):435-42 (2005).

Akinc, et al., "Exploring polyethylenimine-mediated DNA transfection and the proton sponge hypothesis", J Gene Med, . 7(5): 657-63 (2005).

Allard, et al., "Convection-enhanced delivery of nanocarriers for the treatment of brain tumors", Biomaterials, 30(12):2302-18 (2009).

Amoozgar, et al., "Recent advances in stealth coating of nanoparticle drug delivery systems", Wiley Interdiscip Rev Nanomed Nanobiotechnol, 4(2):219-33 (2012).

Beyerle, et al., "PEGylation affects cytotoxicity and cell-compatibility of poly(ethylene imine) for lung application: structure-function relationships", Toxicol Appl Pharmacol, 242(2):146-54 (2010).

Boylan, et al., Enhancement of airway gene transfer by DNA nanoparticles using a pH-responsive block copolymer of polyethylene glycol and poly-L-lysine Biomaterials, 33(7): 2361-71 (2012).

Chirmule, et al., Humoral immunity to adeno-associated virus type 2 vectors following administration to murine and nonhuman primate muscle J Virol, 74(5):2420-5 (2000).

Davies, et al., "Enhanced lung gene expression after aerosol delivery of concentrated pDNA/PEI complexes", Mol Ther, . 16(7):1283-90 (2008).

Dunlap, et al., "Nanoscopic structure of DNA condensed for gene delivery", Nucleic Acids Res, . 25(15):3095-101 (1997).

Hatakeyama, et al., "A multifunctional envelope type nano device (MEND) for gene delivery to tumours based on the EPR effect: a strategy for overcoming the PEG dilem", Adv Drug Deliv Rev, 63(3):152-60 (2011).

(56) References Cited

OTHER PUBLICATIONS

Hu, et al., Effect of PEG conformation and particle size on the cellular uptake efficiency of nanoparticles with the HepG2 cells, J Control Release, 118 (1):7-17 (2007).
Jain, "Nanobiotechnology-based strategies for crossing the blood-brain barrier", Nanomedicine (Lond), 7(8):1225-33 (2012).
Kenny, et al., "Multifunctional receptor-targeted nanocomplexes for the delivery of therapeutic nucleic acids to the brain", Biomaterials, 34(36):9190-200 (2013).
Kim, et al., "Non-degradative intracellular trafficking of highly compacted polymeric DNA nanoparticles", J Control Release, 158(1):102-7 (2012).
Lentz, et al., "Viral vectors for gene delivery to the central nervous system", Neurobiol Dis, 48(2):179-188 (2012).
Lowenstein, et al., "Immune responses to adenovirus and adeno-associated vectors used for gene therapy of brain diseases: the role of immunological synapses in understanding the cell biology of neuroimmune interactions", Curr Gene Ther, 7(5):347-60 (2007).
Lowenstein, et al., "Immunology of neurological gene therapy: how T cells modulate viral vector-mediated therapeutic transgene expression through immunological synapses", Neurotherapeutics, 4(4):715-24 (2007b).
Lutz, et al., "PEG-PEI copolymers for oligonucleotide delivery to cells and tissues", Methods Mol Biol, 433:141-58 (2008).
Mackay, et al., Distribution in brain of liposomes after convection enhanced delivery; modulation by particle charge, particle diameter, and presence of steric coating Brain Res, 1035(2):139-53 (2005).
Malek, et al., "In vivo pharmacokinetics, tissue distribution and underlying mechanisms of various PEI(-PEG)/siRNA complexes", Toxicol Appl Pharmacol, 236(1):97-108 (2009).
Malek, et al., "PEG grafting of polyethylenimine (PEI) exerts different effects on DNA transfection and siRNA-induced gene targeting efficacy", J Drug Target, 16(2):124-39 (2008).
Mastorakos, et al., "Brain penetrating gene vectors for efficient gene transfer to the CNS", Mol Therapy, 22(1):S50 (2014).
Merkel, et al., "In vitro and in vivo complement activation and related anaphylactic effects associated with polyethylenimine and polyethylenimine-graft-poly(ethylene glycol) block copolymers", Biomaterials, 32(21):4936-42 (2011).
Mintzer and Simanek, "Nonviral vectors for gene delivery", Chem Rev, 109(2): 259-302 (2009).
Mishra, et al., "PEGylation significantly affects cellular uptake and intracellular trafficking of non-viral gene delivery particle", Eur J Cell Biol, 83(3):97-111 (2004).
O'Mahony, et al., "Non-viral nanosystems for gene and small interfering RNA delivery to the central nervous system: formulating the solution", J Pharm Sci, 102(10):3469-84 (2013).
Ogris, et al., "DNA/polyethylenimine transfection particles: influence of ligands, polymer size, and PEGylation on internalization and gene expression", AAPS PharmSci, 3(3): E21 (2001).
Olsen and Stein, "New drugs for rheumatoid arthritis", N Engl J Med, . 350(21): 2167-79 (2004).
Pamujula, et al., "Cellular delivery of PEGylated PLGA nanoparticles", J Pharm Pharmacol, 2012. 64(1):61-7 (2012).
Pathak, et al., "Recent trends in non-viral vector-mediated gene delivery", Biotechnol J, 4(11):1559-72 (2009).
Perez-Martinez, et al., "The use of nanoparticles for gene therapy in the nervous system", J Alzheimers Dis, 31(4):697-710 (2012).
Petersen, et al., "Polyethylenimine-graft-poly(ethylene glycol) copolymers: influence of copolymer block structure on DNA complexation and biological activities as gene delivery system", Bioconjug Chem, 13(4):845-54 (2002).
Ruoslahti, "Brain extracellular matrix", Glycobiology, 6(5):489-92 (1996). Sonawane, et al., J Biol Chem, 278(45):44826-31 (2003).
Suk, et al., "Lung Gene Therapy with Highly Compacted DNA Nanoparticles that Overcome the Mucus Barrier", J Control Release, 178:8-17 (2014).
Sun and Zhang, "Cationic polymer optimization for efficient gene delivery", Mini Rev Med Chem, 10(2):108-25 (2010).
Sykova, and Nicholson, "Diffusion in brain extracellular space", Physiol Rev, 88(4):1277-340 (2008).
Thomas, et al., "Progress and problems with the use of viral vectors for gene therapy", Nat Rev Genet, 4(5):346-58 (2003).
Voges, et al., "Imaging-guided convection-enhanced delivery and gene therapy of glioblastoma", Ann Neurol, 54(4):479-87 (2003).
Wohlfart, et al., "Transport of drugs across the blood-brain barrier by nanoparticles", J Control Release, 161(2):264-73 (2012).
Writer, et al., "Lipid peptide nanocomplexes for gene delivery and magnetic resonance imaging in the brain", J Control Release, 162(2):340-8 (2012).
Xiao, et al., "Efficient long-term gene transfer into muscle tissue of immunocompetent mice by adeno-associated virus vector", J Virol, 70(11):8098-108 (1996).
Yurek, et al., "Compacted DNA nanoparticle gene transfer of GDNF to the rat striatum enhances the survival of grafted fetal dopamine neurons", Cell Transplant, 18(10):1183-96 (2009).
Yurek, et al., "Long-term transgene expression in the central nervous system using DNA nanoparticles", Mol Ther, 17(4):641-50 (2009b).
Zimmermann, et al., "Extracellular matrix of the central nervous system: from neglect to challenge", Histochem Cell Biol, 130(4):635-53 (2008).
International Search Report for corresponding PCT application PCT/US2015/030381 dated Aug. 24, 2015.
Nance et al. ("A Dense Poly(ethylene glycol) Coating Improves Penetration of Large Polymeric Nanoparticles within Brain Tissue", 2012).

\* cited by examiner

ENGINEERING SYNTHETIC BRAIN PENETRATING GENE VECTORS

CROSS-REFERENCE TO RELATED APPLICATIONS

This application is a continuation of U.S. application Ser. No. 15/310,535 filed Nov. 11, 2016, which is a 371 application of International Application No. PCT/US2015/030381, filed May 12, 2015, which claims priority to and the benefit of U.S. Ser. No. 61/991,898 filed May 12, 2014, U.S. Ser. No. 61/991,920 filed May 12, 2014 and U.S. Ser. No. 62/001,994 filed May 22, 2014, the contents of which are expressly incorporated hereby by reference in their entirety.

STATEMENT REGARDING FEDERALLY SPONSORED RESEARCH OR DEVELOPMENT

This invention was made with government support under EB003558 and CA164789 awarded by the National Institutes of Health. The government has certain rights in the invention.

FIELD OF THE INVENTION

This invention is generally in the field of gene delivery, and in particular, in delivering nucleic acids across biological barriers using coated particles to penetrate the brain parenchyma and achieve high level widespread transgene expression.

BACKGROUND OF THE INVENTION

Patients with neurological diseases, including Parkinson's disease, Alzheimer's disease, brain tumors and most neurogenetic disorders, suffer from severe debilitating symptoms and lack of therapeutic options that provide curative treatment. The accumulated knowledge of specific genetic targets that can alter or reverse the natural history of central nervous system (CNS) diseases has rendered gene therapy an attractive therapeutic strategy [O'Mahony, A. M., et al., *J Pharm Sci*, 2013. 102(10): 3469-3484; Lentz, et al., *Neurobiol Dis*, 2012. 48(2): 179-188.]. Multiple preclinical and clinical studies have aimed to improve the delivery of nucleic acids to the CNS using leading viral or non-viral gene vectors with specific focus to enhancing the level and distribution of transgene expression throughout the brain tissue [O'Mahony, et al., *J Pharm Sci*, 2013. 102(10): 3469-3484; Perez-Martinez, et al., *J Alzheimers Dis*, 2012. 31(4): 697-710].

Viral gene vectors, though relatively efficient, have been limited by one or more drawbacks, including low packaging capacity, technical difficulties in scale-up, high cost of production [Thomas, et al., *Nat Rev Genet*, 2003. 4(5): 346-358.] and risk of mutagenesis [Olsen and Stein, *N Engl J Med*, 2004. 350(21): 2167-2179.]. Furthermore, despite the immune privileged nature of the CNS, neutralizing immune responses may occur secondary to repeated administrations or prior exposures [Lentz, et al., *Neurobiol Dis*, 2012. 48(2): 179-188; Xiao, X., et al., *J Virol*, 1996. 70(11): 8098-8108; Chirmule, N., et al., *J Virol*, 2000. 74(5): 2420-2425; Lowenstein, P. R., et al., *Curr Gene Ther*, 2007. 7(5): p. 347-60; Lowenstein, P. R., et al., *Neurotherapeutics*, 2007. 4(4): 715-724; Voges, J., et al., *Ann Neurol*, 2003. 54(4): 479-487.].

Non-viral gene vectors can offer an attractive alternate strategy for gene delivery without many of these limitations [O'Mahony, A. M., et al., *J Pharm Sci*, 2013. 102(10): 3469-3484]. Cationic polymer-based gene vectors provide a tailorable platform for DNA condensation and efficient gene transfer in vitro and in vivo. Their positive charge density allows for stable compaction of negatively charged nucleic acids [Sun, X. and N. Zhang, *Mini Rev Med Chem*, 2010, 10(2): 108-125; Dunlap, D. D., et al., *Nucleic Acids Res*, 1997. 25(15): 3095-3101] and protects them from enzymatic degradation [Kukowska-Latallo, J. F., et al., *Hum Gene Ther*, 2000. 11(10): 1385-1395.]. Also, the number of protonable amines provides increased buffering capacity that facilitates endosome escape via the "proton sponge effect", leading to efficient transfection [Akinc, A., et al., *J Gene Med*, 2005. 7(5): 657-663]. A wide variety of cationic polymers have been developed for this purpose, offering gene vectors with diverse physicochemical profiles and in vivo behaviors [Mintzer, M. A. and E. E. Simanek. *Chem Rev*, 2009. 109(2): 259-302; Pathak, et al., *Biotechnol J*, 2009. 4(11): 1559-72.].

However, non-viral gene vectors still face a number of barriers prior to reaching the target cells in the brain [O'Mahony, et al., *J Pharm Sci*, 2013. 102(10): 3469-3484]. Various strategies have been developed to manipulate or bypass the blood brain barrier (BBB) [Jain, *Nanomedicine* (Lond), 2012. 7(8): 1225-33; Wohlfart, et al., *J Control Release*, 2012. 161(2): 264-273.], which is the primary barrier to the systemic delivery of gene vectors to the brain. These approaches include, but are not limited to, direct, local administration to the CNS [Patel, et al., *Advanced Drug Delivery Reviews*, 2012. 64(7):701-705] and reversible disruption of the BBB via focused ultrasound [Vykhodtseva, et al., *Ultrasonics*, 2008. 48(4): 279-296] or chemical reagents [Kroll, et al., *Neurosurgery*, 1998. 42(5): 1083-1099; discussion 1099-100.]. However, once beyond the BBB, the anisotropic and electrostatically charged extracellular matrix (ECM) found between brain cells has been widely recognized as another critical barrier [Nance, et al., *Sci Transl Med*, 2012. 4(149): 149ra119; Sykova, et al., *Physiol Rev*, 2008. 88(4): 1277-1340; Zamecnik, J., *Acta Neuropathol*, 2005. 110(5):435-442]. This 'brain tissue barrier', regardless of administration method, hampers widespread distribution of macromolecules and nanoparticles in the brain, thereby limiting their coverage throughout the disseminated target area of neurological diseases [Voges, J., et al., *Ann Neurol*, 2003. 54(4): 479-487; Nance, E. A., et al., *Sci Transl Med*, 2012. 4(149): 149ra119; Sykova, et al., *Physiol Rev*, 2008. 88(4): 1277-340; MacKay, et al., *Brain Res*, 2005. 1035(2): 139-153]. The ECM is rich in hyaluronan, chondroitin sulfate, proteoglycans, link proteins and tenascins and may provide a negatively charged adhesive barrier to the penetration of cationic polymeric gene vectors [Sykova, et al., *Physiol Rev*, 2008. 88(4): 1277-1340; Zimmermann, et al., *Histochem Cell Biol*, 2008. 130(4): 635-653]. Moreover, the pore size of the ECM imposes a steric barrier for the movement of nanoparticles in the CNS with non-adhesive 114 nm, but not 200 nm, particles able to penetrate the brain tissue [Nance, E. A., et al., *Sci Transl Med*, 2012. 4(149): p. 149ra119; Kenny, G. D., et al., *Biomaterials*, 2013. 34(36): 9190-9200. It has been shown that sub-100 nm nanoparticles exceptionally well-coated with hydrophilic and neutrally charged polyethylene glycol (PEG) rapidly diffuse in the brain ECM allowing the Widespread distribution of therapeutics [Nance, E. A., et al., *Sci Transl Med*, 2012. 4(149): p. 149ra119].

Convection enhanced delivery (CED) can be applied to further enhance the distribution of therapeutics by providing a pressure gradient during intracranial administration [Allard, et al., *Biomaterials*, 2009. 30(12): 2302-2318.]. However, CED is unlikely to provide a significant benefit if particles remain entrapped in the brain parenchyma due to adhesive interactions and/or steric obstruction. Thus, physicochemical properties of particles that allow unhindered diffusion in the brain parenchyma remain critical for achieving enhanced particle penetration following CED [Allard, et al., *Biomaterials*, 2009. 30(12): 2302-18; Kenny, et al., *Biomaterials*, 2013. 34(36): 9190-9200]. However, even following CED, the interactions between positively charged gene vectors and the negatively charged ECM, confine cationic nanoparticles to the point of injection and perivascular spaces, and limit their penetration into the brain parenchyma [MacKay, et al., *Brain Res*, 2005. 1035(2): 139-153; Kenny, et al., *Biomaterials*, 2013. 34(36): 9190-9200; Writer, et al., *J Control Release*, 2012. 162(2): p. 340-8.].

It is therefore an object of the present invention to provide optimized physicochemical properties of stable gene vectors that can penetrate the brain parenchyma thus improving distribution and transgene expression throughout the brain tissue.

It is a further object of the present invention to provide gene delivery vectors with a favorable safety profile.

It is a yet further object of the present invention to combine nanoparticles with delivery strategies that can further enhance their distribution and transgene expression in the tissue, especially the brain.

SUMMARY OF THE INVENTION

A synthetic gene delivery platform with a dense surface coating of hydrophilic and neutrally charged hydrophilic polymer such as polyethylene glycol ("PEG") or polaxamer (polyethylene glycol or polyalkylene oxid copolymers, PLURONIC®), capable of rapid diffusion and widespread distribution in brain tissue, and highly effective gene delivery to target cells therein has been developed. Examples demonstrate densely PEGylated gene vectors, formulated from a mixture of cationic polymers, such as 25 kDa polyethylenimine (PEI) or poly-L lysine (PLL), and the hydrophilic polymers conjugated to polymers such as PEG, rapidly penetrate the brain parenchyma. Convection enhanced delivery (CED) of these brain penetrating gene vectors provides an enhanced distribution of the gene vectors, resulting in highly effective transgene expression throughout the brain tissue.

The nanoparticles are formed from a blend of free polymer and polymer conjugated to a hydrophilic polymer such as polyethylene glycol. The blending technique significantly improves nanoparticle compaction and increases colloidal stability in high ionic strength solutions, including artificial cerebrospinal fluid. This strategy has been further applied to develop peptide and biodegradable polymer based brain penetrating gene vectors with similar attributes. As described in the examples, nanoparticles including nucleic acid, a biocompatible, biodegradable cationic polymer and polyethylene glycol, wherein between 90% and 75% of the cationic polymer are conjugated to polyethylene glycol, and the nucleic acids are encapsulated within and/or are associated with the surface of the nanoparticles. The nanoparticles are coated with polyethylene glycol at a density that imparts a near neutral charge and optimizes rapid diffusion through the brain parenchyma. The nanoparticles preferably have a diameter of less than 114 nm, for example, 50 nm.

In some embodiments the cationic polymer or polyethylene glycol is branched. Branching enhances the amount of polyethylene glycol conjugated to the polymer, for example, by at least three times as much polyethylene glycol, as compared to conjugation of non-branched polyethylene glycol and non-branched polymer. In some embodiments the polyethylene glycol has a molecular weight between 1,000 Daltons and 10,000 Daltons, such as 5,000 Daltons.

In certain embodiments the cationic polymer is branched polyethyleneimine with a molecular weight between 10,000 Daltons and 50,000 Daltons, for example 25,000 Daltons. In further embodiments the molar ratio of polyethylene glycol to polyethyleneimine is more than 8, preferably 26. In a particular embodiment 25% of the total amines derive from unconjugated branched polyethyleneimine. In other embodiments, the cationic polymer is poly-L lysine and the polyethylene glycol is branched polyethylene glycol with a molecular weight of 5,000 Daltons. In one embodiment, 90% of the total poly-L lysine is conjugated with polyethylene glycol.

Dosage formulations for the delivery of a therapeutic or prophylactic nucleic acid to the brain are also disclosed. The formulations include a therapeutically effective amount of nanoparticles densely coated with polyethylene and a pharmaceutically acceptable excipient for delivery into the brain. The nanoparticles can be formulated for direct or indirect injection into the brain.

Methods of making nanoparticles densely coated with polyethylene glycol for the delivery of nucleic acids to the brain are also provided. The methods include preparing a blended polymer by mixing free polymer with polymer conjugated to a polymer such as polyethylene glycol, adding the nucleic acid to the blended polymer and purifying the nanoparticles.

Methods for treating a disease or disorder of the brain, including administering to the brain a formulation including a therapeutically effective amount of the nanoparticles to alleviate one or more symptoms of a disease or disorder of the brain and a pharmaceutically acceptable excipient for delivery into the brain are also provided. The formulation can be administered directly or indirectly to the brain. In some embodiments the formulation is administered systemically and the nanoparticles penetrate the brain by passing through the blood-brain barrier. The particles can be administered in combination with one or more techniques to bypass the blood brain barrier. Exemplary techniques include convection enhanced delivery (CED), electron paramagnetic resonance, ultrasound, and ultrasound application with microbubbles. Other methods of increasing uptake into the brain include formulating with an osmotic agent such as mannitol. The methods can be useful to treat one or more symptoms of a disease or disorder including, but not limited to, tumors, neurological disorders, and brain injury or trauma.

BRIEF DESCRIPTION OF THE DRAWINGS

FIGS. 2A-2C show the % cell viability of rabbit primary astrocytes (FIG. 2A), rat primary astrocytes (FIG. 2B) and 9 L rat gliosarcoma cells (FIG. 2C), respectively, treated with various concentrations (1 mg/ml, 5 mg/ml or 10 mg/ml) of PEI nanoparticles (UPN, CPN and BPN) or PEG-PLL nanoparticles, respectively. Cell viability was measured after 24 hr of treatment and compared to non-treated controls. Data represents the mean±SEM. * Denotes statistically significant (p<0.05) difference from 100%. FIG. 2D shows histopathology (inflammation and hemorrhage), scored using a custom scale (0: no inflammation or hemorrhage; 1: mild; 2: moderate; 3: severe) for each of the PEI nanoparticles (UPN, CPN and BPN) or saline control (Ctrl), respectively.

FIGS. 3A and 3B show the % cell uptake of 9 L rat gliosarcoma cells (FIG. 3A) and rat primary astrocytes (FIG. 3B), treated with PEI nanoparticles (UPN, CPN and BPN), PEG-PLL nanoparticles, or saline control (Ctrl), respectively. FIGS. 3C and 3D show luciferase activity (RLU)/mg protein following in vitro transfection of luciferase gene into 9 L rat gliosarcoma cells (FIG. 3C) and rat primary astrocytes (FIG. 3D), treated with PEI nanoparticles (UPN, CPN and BPN), PEG-PLL nanoparticles, or saline control (Ctrl), respectively. Data represents the mean±SEM. * Denotes statistical significance P<0.05.

DETAILED DESCRIPTION OF THE INVENTION

I. Definitions

Figure 1:
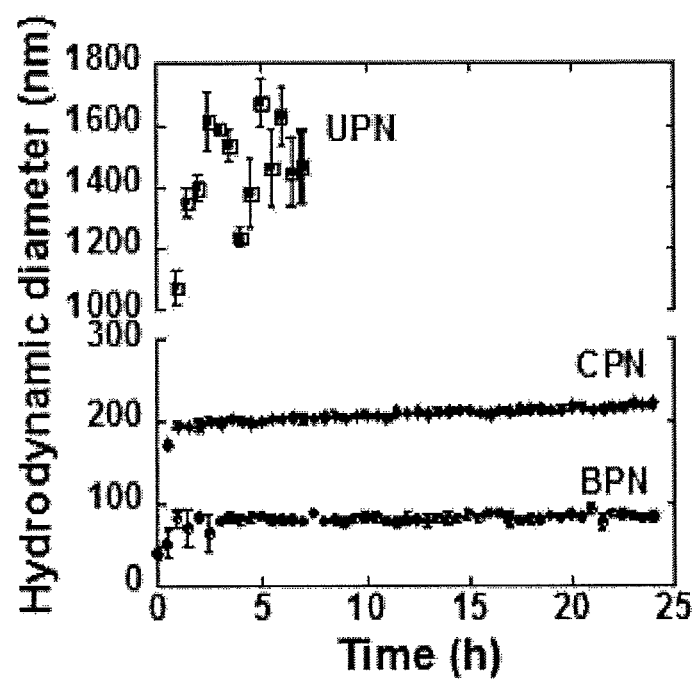
FIG. 1 is a graph showing the hydrodynamic diameter of vectors (nm) over time (hours) for UPN (■), CPN (+) and BPN (♦), respectively. Size was measured by dynamic light scattering (DLS) in aCSF at pH 7.0. Measurements continued for 24 hours every half an hour or until polydispersity (PDI)>0.5. Data represents the mean±SEM.

The terms "biocompatible" as used herein refers to one or more materials that are neither themselves toxic to the host (e.g., an animal or human), nor degrade (if the polymer degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the polymer into smaller, non-polymeric subunits.

The term "corresponding particle" or "reference particles" as used herein refers to a particle that is substantially identical to another particle to which it is compared, but typically lacking a surface modification to promote transport differences through the pores in the ECM of the brain. A corresponding particle is typically of similar material, density, and size as the particle to which it is compared. In certain embodiments, a corresponding particle is a particle that does not have a dense coating of polyethylene glycol. In certain embodiments, a comparable particle is a particle that is not formed of a blended mixture containing free polymer and polymer conjugated to polyethylene glycol.

The term "densely coated particle" refers to a particle that is modified to specifically enhance the density of coating agent at the surface of the particle, for example, relative to a reference particle. In some embodiments, a densely coated particle is formed from a ratio of polyethylene glycol to polymer that is sufficient to alter the physicochemical properties of the particle relative to a less densely coated, or non-coated particle. In some embodiments, the density of coating agent is sufficient to completely mask the charge of the particle, resulting in a near neutral charge and near neutral zeta potential value and colloidal stability in physiological solutions. In a particular embodiment, a densely coated particle is achieved using branched polyethylene glycol or branched polymer, wherein the branching enhances the ratio of polyethylene glycol to polymer as compared to a reference particle that does not contain a branched polymer or branched polyethylene glycol.

The term "nucleic acids" refers to isolated DNA, cDNA, RNA, miRNA, siRNA, plasmids, vectors, and expression constructs.

The term "diameter" is art-recognized and is used herein to refer to either of the physical diameter or the hydrodynamic diameter. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles.

"Sustained release" as used herein refers to release of a substance over an extended period of time in contrast to a bolus type administration in which the entire amount of the substance is made biologically available at one time.

The term "microspheres", "microparticles", and "microcapsules" are used interchangeably unless otherwise stated. These have a size between about one up to about 1000 microns. In general, "microcapsules," have a core of a different material than the shell material. A microparticle may be spherical or nonspherical and may have any regular or irregular shape. If the structures are less than about one micron in diameter, then the corresponding art-recognized terms "nanosphere," "nanocapsule," and "nanoparticle" may be utilized. In certain embodiments, the nanospheres, nanocapsules and nanoparticles have an average diameter of about 100 nm, or less than 100 nm, such as 50 nm, or 10 nm.

A composition comprising microparticles or nanoparticles may include particles of a range of particle sizes. In certain embodiments, the particle size distribution may be uniform, e.g., within less than about a 20% standard deviation of the median volume diameter, and in other embodiments, still more uniform, e.g., within about 10% of the median volume diameter.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrasternal injection and infusion.

The term "surfactant" refers to an agent that lowers the surface tension of a liquid.

The term "therapeutic agent" refers to an agent that can be administered to prevent or treat a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refer to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including chemically or physically couple, in physical admixture, or enveloping the agent in a coating layer

II. Compositions

Synthetic gene delivery platforms with a dense surface coating of hydrophilic and neutrally charged polymer such as polyethylene glycol (PEG) or polyethylene glycol-polyoxyethylene block copolymer known as poloxamer such as a PLURONIC® (referred to collectively as "PEGylated gene vectors") which are capable of rapid diffusion and widespread distribution in brain tissue are disclosed.

A. Nanoparticles

In some embodiments the densely PEGylated gene vectors are nanoparticles formulated from a mixture of unconjugated and polyethylene glycol (PEG) conjugated cationic polymers. The nanoparticles rapidly penetrate the brain parenchyma and have reduced cytotoxicity and increased colloidal stability in high ionic strength solutions, relative to less-densely PEGylated gene vectors.

1. Coating Agents

Nanoparticles, coated with one or more materials that promote diffusion of the particles through the ECM in the brain by reducing interactions between the particles and brain tissue (e.g., surface altering agents), are disclosed. Examples of the surface-altering agents include, but are not limited to, polyethylene glycol ("PEG") and poloxomers (polyethylene oxide block copolymers).

i. Polyethylene Glycol (PEG)

A preferred coating agent is poly(ethylene glycol), also known as PEG. PEG may be employed to reduce adhesion in brain ECM in certain configurations, e.g., wherein the length of PEG chains extending from the surface is controlled (such that long, unbranched chains that interpenetrate into the ECM are reduced or eliminated). For example, linear high MW PEG may be employed in the preparation of particles such that only portions of the linear strands extend from the surface of the particles (e.g., portions equivalent in length to lower MW PEG molecules). Alternatively, branched high MW PEG may be employed. In such embodiments, although the molecular weight of a PEG molecule may be high, the linear length of any individual strand of the molecule that extends from the surface of a particle would correspond to a linear chain of a lower MW PEG molecule.

Representative PEG molecular weights in daltons (Da) include 300 Da, 600 Da, 1 kDa, 2 kDa, 3 kDa, 4 kDa, 5 kDa, 6 kDa, 8 kDa, 10 kDa, 15 kDa, 20 kDa, 30 kDa, 50 kDa, 100 kDa, 200 kDa, 500 kDa, and 1 MDa. In preferred embodiments, the PEG has a molecular weight of about 5,000 Daltons. PEG of any given molecular weight may vary in other characteristics such as length, density, and branching. In a particular embodiment, a coating agent is methoxy-PEG-amine, with a MW of 5 kDa. In another embodiment, a coating agent is methoxy-PEG-N-hydroxysuccinimide with a MW of 5 kDa (mPEG-NHS 5 kDa).

In alternative embodiments, the coating is a poloxamer such as the polyethylene glycol-polyethylene oxide block copolymers marketed as PLUORONICs®.

iii. Density of Coating Agent

In preferred embodiments the nanoparticles are coated with PEG or other coating agent at a density that optimizes rapid diffusion through the brain parenchyma. The density of the coating can be varied based on a variety of factors including the material and the composition of the particle.

In a preferred embodiment the co-polymer molar ratio of PEG or other coating agent to cationic polymer is greater than 8 (i.e., more than 8 moles of PEG to every mole of cationic polymer). The ratio by moles of PEG or other coating agent to cationic polymer can be 9, 10, 11, 12, 13, 14 15, 16, 17, 18, 19, 20, 21, 22, 23, 24, 25, 26, 27, 28, 29, 30, 37, 50 or more than 50. A preferred molar ratio of PEG or other coating agent to cationic polymer is 26.

In one embodiment, the density of the PEG or other coating agent is at least 0.001, 0.002, 0.005, 0.01, 0.02, 0.05, 0.1, 0.2, 0.5, 1, 2, 5, 10, 20, 50, or 100 units per $nm^2$.

In another embodiment, the amount of the PEG or other coating agent is expressed as a percentage of the mass of the particle. In a particular embodiment, the mass of the PEG or other coating agent is at least $1/10,000$, $1/7500$, $1/5000$, $1/4000$, $1/3400$, $1/2500$, $1/2000$, $1/1500$, $1/1000$, $1/500$, $1/250$, $1/200$, $1/150$, $1/100$, $1/75$, $1/50$, $1/25$, $1/20$, $1/5$, $1/2$, or $9/10$ of the mass of the particle. In a further embodiment, the weight percent of the PEG or other coating agent is at least 80%, 81%, 82%, 83%, 84%, 85%, 86%, 87%, 88%, 89%, 90%, 91%, 92%, 93%, 94%, 95%, or greater.

2. Core Polymer

Any number of biocompatible polymers can be used to prepare the nanoparticles. In preferred embodiments, the biocompatible polymer(s) is a cationic polymer. The cationic polymer can be a branched polymer, to enhance the capacity of the polymer to conjugate to a coating agent such as PEG. In some embodiments, the biocompatible polymer(s) is biodegradable.

i. Types of Polymers

Exemplary cationic polymers include, but are not limited to, cyclodextrin-containing polymers, in particular cationic cyclodextrin-containing polymers, such as those described in U.S. Pat. No. 6,509,323, polyethylenimine (PEI), poly(L-lysine) (PLL), polyethylenimine (PEI), polymethacrylate, chitosan, poly(glycoamidoamine), schizophyllan, DEAE-dextran, dextran-spermine, poly(amido-amine) (PAA), poly (4-hydroxy-L-proline ester), poly[R-(4-aminobutyl)-L-glycolic acid] (PAGA), poly(amino-ester), poly(phosphazenes) (PPZ), poly(phosphoesters) (PPE), poly(phosphoramidates) (PPA), TAT-based peptides, Antennapedia homeodomain peptide, MPG peptide, poly(propylenimine), carbosilane, and amine-terminated polyaminophosphine. In a particular embodiment the polymer is a cationic polymer with multiple free amines. Preferred polymers include polyethylenimine (PEI) and poly-L-lysine (PLL). Copolymers of two or more polymers described above, including block and/or random copolymers, may also be employed to make the polymeric particles.

ii. Branched Polymers

In polymer chemistry, branching occurs by the replacement of a substituent, e.g., a hydrogen atom, on a monomer subunit, by another covalently bonded chain of that polymer; or, in the case of a graft copolymer, by a chain of another type. Branching may result from the formation of carbon-carbon or various other types of covalent bonds. Branching by ester and amide bonds is typically by a condensation reaction, producing one molecule of water (or HCl) for each bond formed.

The branching index measures the effect of long-chain branches on the size of a macromolecule in solution. It is defined as $g=<sb2>/<sl2>$, where sb is the mean square radius of gyration of the branched macromolecule in a given solvent, and sl is the mean square radius of gyration of an otherwise identical linear macromolecule in the same solvent at the same temperature. A value greater than 1 indicates an increased radius of gyration due to branching.

In preferred embodiments, the core polymer or PEG is a branched polymer that is capable of enhancing conjugation of the coating agent and core polymer. Exemplary branched polymers include 25 kDa branched polyethyleneimine (PEI) and 5 kDa branched methoxy-PEG.

iii. Copolymers

In preferred embodiments, copolymers of PEG or derivatives thereof with any of the polymers described above may be used to make the polymeric particles. In certain embodiments, the PEG or derivatives may locate in the interior positions of the copolymer. Alternatively, the PEG or derivatives may locate near or at the terminal positions of the copolymer. In certain embodiments, the nanoparticles are formed under conditions that allow regions of PEG to phase separate or otherwise locate to the surface of the particles. The surface-localized PEG regions alone may perform the function of, or include, a surface-altering agent.

3. Nucleic Acids

Nanoparticle gene carriers typically carry one or more nucleic acids. The nucleic acid can alter, correct, or replace an endogenous nucleic acid sequence. In preferred embodiments, the nucleic acid is used to treat cancers, correct defects in genes in brain diseases and metabolic diseases affecting brain function, genes such as those for the treatment of Parkinsons and ALS.

Gene therapy is a technique for correcting defective genes responsible for disease development. Researchers may use one of several approaches for correcting faulty genes:

A normal gene may be inserted into a nonspecific location within the genome to replace a nonfunctional gene. This approach is most common.

An abnormal gene could be swapped for a normal gene through homologous recombination.

The abnormal gene could be repaired through selective reverse mutation, which returns the gene to its normal function.

The regulation (the degree to which a gene is turned on or off) of a particular gene could be altered.

The nucleic acid carried by the nanoparticle gene carrier can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. For example, the nucleic acid can be custom synthesized to contain properties that are tailored to fit a desired use. Common modifications include, but are not limited to, use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the non-bridging oxygens is replaced by sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD). The latter methods avoid the problem of elemental sulfur's insolubility in most organic solvents and the toxicity of carbon disulfide. The TETD and BDTD methods also yield higher purity phosphorothioates. (See generally Uhlmann and Peymann, 1990, Chemical Reviews 90, at pages 545-561 and references cited therein, Padmapriya and Agrawal, 1993, Bioorg. & Med. Chem. Lett. 3, 761).

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, and amino spacers such as 8-amino-3,6-dioxaoctanoic acid (referred to herein as O-linkers). Methods for the chemical assembly of PNAs are well known. See, for example, U.S. Pat. Nos. 5,539,082, 5,527,675, 5,623,049, 5,714,331, 5,736,336, 5,773,571 and 5,786,571.

In some embodiments, the nucleic acid includes one or more chemically-modified heterocyclic bases including, but not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladeno sine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to, O-methyl, amino-, and fluoro-modified analogs Inhibitory RNAs modified with 2'-flouro (2'-F) pyrimidines appear to have favorable properties in vitro. Moreover, one report suggested 2'-F modified siRNAs have enhanced activity in cell culture as compared to 2'-OH containing siRNAs. 2'-F modified siRNAs are functional in mice but that they do not necessarily have enhanced intracellular activity over 2'-OH siRNAs.

In some embodiments the nucleic acid includes one or more sugar moiety modifications, including, but not limited to, 2'-O-aminoethoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA).

Nanoparticle gene carriers carrying one or more nucleic acid can be utilized to deliver nucleic acid cargo in a method of gene therapy. Methods of gene therapy typically rely on the introduction into the cell of a nucleic acid molecule that alters the genotype of the cell. For example, corrective genes can be introduced into a non-specific location within the host's genome. This approach typically requires delivery systems to introduce the replacement gene into the cell, such as genetically engineered viral vectors.

In other embodiments, functional nucleic acids are introduced to prevent the function or expression of a particular gene that causes a defect or disease.

Functional nucleic acids are nucleic acid molecules that have a specific function, such as binding a target molecule or catalyzing a specific reaction. For example, functional nucleic acids include, but are not limited to, antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

In a particular embodiment, the inhibitory nucleic acids are antisense nucleic acids. Antisense molecules are designed to interact with a target nucleic acid molecule through either canonical or non-canonical base pairing. The interaction of the antisense molecule and the target molecule promotes the destruction of the target molecule through, for example, RNAseH mediated RNA-DNA hybrid degradation. Alternatively the antisense molecule interrupts a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Triplex forming functional nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett. 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

An miRNA or pre-miRNA can be 18-100 nucleotides in length, and more preferably from 18-80 nucleotides in length. Mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation.

Given the sequence of an miRNA or a pre-miRNA, an miRNA antagonist that is sufficiently complementary to a portion of the miRNA or a pre-miRNA can be designed according to the rules of Watson and Crick base pairing. As used herein, the term "sufficiently complementary" means that two sequences are sufficiently complementary such that a duplex can be formed between them under physiologic conditions. An miRNA antagonist sequence that is sufficiently complementary to an miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In a preferred embodiment, the miRNA antagonist is 100% complementary to an miRNA or pre-miRNA target sequence. In some embodiments, the miRNA antagonist is complementary to a portion of the miRNA or pre-miRNA sequence of a human. Sequences for miRNAs are available publicly, for example, through the miRBase registry (Griffiths-Jones, et al., *Nucleic Acids Res.*, 36(Database Issue):D154-D158 (2008); Griffiths-Jones, et al., *Nucleic Acids Res.*, 36(Database Issue):D140-D144 (2008); Griffiths-Jones, et al., *Nucleic Acids Res.*, 36(Database Issue):D109-D111 (2008)) and other publically accessible databases.

In some embodiments, there will be nucleotide mismatches in the region of complementarity. In a preferred embodiment, the region of complementarity will have no more than 1, 2, 3, 4, or 5 mismatches.

In one embodiment, the miRNA antagonists are oligomers or polymers of ribonucleic acid (RNA) or deoxyribonucleic acid (DNA) or modifications thereof. miRNA antagonists include oligonucleotides that contain naturally-occurring nucleobases, sugars and covalent internucleoside (backbone) linkages.

In some embodiments, the miRNA antagonists are antagomirs. Antagomirs are a specific class of miRNA antagonists that are described, for example, in US2007/0213292 to Stoffel et al. Antagomirs are RNA-like oligonucleotides that contain various modifications for RNase protection and pharmacologic properties such as enhanced tissue and cellular uptake. Antagomirs differ from normal RNA by having complete 2'-O-methylation of sugar, phosphorothioate backbone and a cholesterol-moiety at 3'-end.

Antagomirs can include a phosphorothioate at least the first, second, or third internucleotide linkage at the 5' or 3' end of the nucleotide sequence. In one embodiment, antagomirs contain six phosphorothioate backbone modifications; two phosphorothioates are located at the 5'-end and four at the 3'-end. Phosphorothioate modifications provide protection against RNase activity and their lipophilicity contributes to enhanced tissue uptake.

Examples of antagomirs and other miRNA inhibitors are described in WO2009/020771, WO2008/091703, WO2008/046911, WO2008/074328, WO2007/090073, WO2007/027775, WO2007/027894, WO2007/021896, WO2006/093526, WO2006/112872, WO2007/112753, WO2007/112754, WO2005/023986, or WO2005/013901, all of which are hereby incorporated by reference.

Custom designed Anti-miR™ molecules are commercially available from Applied Biosystems. Thus, in some embodiments, the antagomir is an Ambion® Anti-miR™ inhibitor. These molecules are chemically modified and optimized single-stranded nucleic acids designed to specifically inhibit naturally occurring mature miRNA molecules in cells.

Custom designed Dharmacon Meridian™ microRNA Hairpin Inhibitors are also commercially available from Thermo Scientific. These inhibitors include chemical modifications and secondary structure motifs. For example, Vermeulen et al. reports in US2006/0223777 the identification of secondary structural elements that enhance the potency of these molecules. Specifically, incorporation of highly structured, double-stranded flanking regions around the reverse complement core significantly increases inhibitor function and allows for multi-miRNA inhibition at subnanomolar concentrations. Other such improvements in antagomir design are contemplated for use in the disclosed methods.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oigonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule. The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased flexibility over methods of induced recombination such as triple-helix oligonucleotides and bis-peptide nucleic acids which require a polypurine sequence in the target double-stranded DNA.

The molar ratio of the nucleic acid to the core polymer within the nanoparticles can be at least 0.5, 1, 10, 100, 1000 or more than 1000.

4. Additional Active Agents

Nanoparticle gene carriers may carry only "genetic" materials, or other therapeutic, prophylactic and/or diagnostic agents can be co-delivered depending on the application. However, any "genetic" materials that can perform the listed functions can be packaged into the nanoparticles. For example, tumor suppressor genes such as p53 and Rb can be complexed into nanoparticles to be used for cancer patients, so as any plasmid DNA or siRNA that possess anti-inflammatory, anti-viral functions, etc.

These additional; active agents can be dispersed in the nanoparticle gene carriers or be covalently attached to one or more of the polymeric components of the nanoparticle.

Suitable additional active agents include, but are not limited to, other nucleic acid-based medicine, anti-inflammatory drugs, antiproliferatives, chemotherapeutics, vasodilators, and anti-infective agents. In certain embodiments, the nanoparticle gene carriers contain one or more antibiotics, such as tobramycin, colistin, or aztreonam. The disclosed nanoparticle gene carriers can optionally contain one or more antibiotics which are known to possess anti-inflammatory activity, such as erythromycin, azithromycin, or clarithromycin. Nanoparticles may also be used for the delivery of chemotherapeutic agents, and anti-proliferative agents.

5. Nanoparticle Properties

As shown in the examples, the disclosed nanoparticles diffuse through the pores of the ECM of the brain at a greater rate of diffusivity than a reference nanoparticle, such as an uncoated particle, e.g., uncoated PEI particle.

i. Particle Diffusivity

The disclosed nanoparticles may pass through the pores of the ECM of the brain at a rate of diffusivity that is at least 5, 10, 20, 30, 50, 60, 80, 100, 125, 150, 200, 250, 500, 600, 750, 1000, 1500, 2000, 2500, 3000, 4000, 5000, 10000- or greater fold higher than a reference particle.

The transport rates of the particles can be measured using a variety of techniques in the art. In one embodiment, the rate of diffusion is measured by geometric ensemble mean squared displacements (MSD). In a particular embodiment, the particles may diffuse through the pores of the ECM of the brain with an MSD that is at least 5, 10, 20, 30, 50, 60, 80, 100, 125, 150, 200, 250, 500, 600, 750, 1000, 1500, 2000, 2500, 3000, 4000, 5000, 10000- or greater fold higher than a reference particle.

In other embodiments, the disclosed nanoparticles diffuse through the pores of the ECM of the brain at a rate approaching the rate of diffusivity at which the particles diffuse through water. In a particular embodiment, the rate of diffusivity is at least $1/1000$, $1/800$, $1/700$, $1/600$, $1/500$, $1/400$, $1/250$, $1/200$, $1/150$, $1/100$, $1/75$, $1/50$, $1/25$, $1/10$, $1/7$, $1/5$, $1/2$, or 1 times the rate of diffusivity of the particle in water under identical conditions. For example, at a time scale of 1 s, the rates of diffusion of unmodified or reference particles can be slower in brain tissue than the same particles in water.

The density of coating of PEG or other material can affect the diffusion of nanoparticle within brain parenchyma. In some embodiments the MSD at 1 sec of densely PEGylated particles is at least 5-fold greater than that of less-densely PEGylated particles, or at least 29-fold higher than that of non-PEGylated particles. In further embodiments, the mean square displacement (MSD) at 1 sec of densely PEGylated particles is only 260-fold or less slower in brain tissue than in artificial cerebral spinal fluid (aCSF), whereas less-densely PEGylated particles can be up to 930-fold slower and non-PEGylated particles can be up to 6,900-fold slower. In a particular embodiment, at least 63% of densely PEGylated nanoparticles are capable of movement through rat brain parenchyma, relative to 32.9% of less-densely PEGylated particles and 10.3% of non-PEGylated particles, respectively.

The heterogeneity in particle transport rates can also be evaluated by examining the distribution of individual particle diffusivities over a particular time period, e.g., 1 s. In one embodiment, at least 15%, 20%, 25%, 30%, 35%, 40%, 45%, 50%, 55%, 60%, 65%, 70%, 75%, 80%, or greater of coated particles of a given average particle size are classified as diffusive.

ii. Electro-Kinetic Potential

The presence of the PEG or coating agent can affect the zeta-potential of the particle. In one embodiment, the zeta potential of the particles is between −10 mV and 100 mV, between −10 and 50 mV, between −10 mV and 25 mV, between −5 mV and 20 mV, between −10 mV and 10 mV, between −10 mV and 5 mV, between −5 mV and 5 mV, or between −2 mV and 2 mV. In a preferred embodiment, the surface charge is near neutral.

iii. Particle Size

In some embodiments, the disclosed nanoparticles have an average diameter equal to or smaller than the pores in the ECM of the brain. In particular embodiments, the particles have an average diameter from about 40 nm up to about 150 nm, up to about 100 nm, or up to about 60 nm, more preferably about 50 nm. Particle size can be measured using any technique known in the art, for example using dynamic light scattering. Particle size may also be referenced with respect to a population, wherein a percentage of 60, 65, 70, 75, 80, 85, 90, 95% of the particles have diameters within the specified range.

In another embodiment, the particles have an average diameter such that a majority of the particles do not become localized within cells or micro-domains within tissue compared to larger particles. As shown in the Table 1, particles having an average particle size of 50 nm showed a larger MSD at 1 sec when densely PEGylated, as measured using multiple particle tracking (MPT) of fluorescently labeled gene vectors in rodent brain.

In certain embodiments the nanoparticles release an effective amount of the nucleic acids over a period of at least 10 minutes, 20 minutes, 30 minutes, one hour, two hours, hour hours, six hours, ten hours, one day, three days, seven days, ten days, two weeks, one month, or longer.

iv. Toxicity

The disclosed nanoparticles densely-coated with PEG or other coating agents are less toxic than non-coated or conventionally coated particles. The in vitro or in vivo toxicity of nanoparticles can be assessed using any technique known in the art, such as cell viability assays. In some embodiments, toxicity of the particles is associated with the ratio of polymer to DNA. For example, a ratio of polymer to DNA of 1, or 2, or 3, or 4, can be less toxic than a ratio of polymer to DNA greater than 4, such as a ratio of 5 or more.

The toxicity of the nanoparticles can be dependent upon the cell-type or tissue-type and can depend upon the concentration of the nanoparticles. In some embodiments toxicity is considered low when 75% of normal primary cells are viable following exposure to nanoparticles at a concentration of 10 µg/ml for two hours.

B. Pharmaceutical Excipients for Delivery to the Brain

The particles may be administered in combination with a physiologically or pharmaceutically acceptable carrier, excipient, or stabilizer. Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. In preferred embodiments, the particles are formulated for parenteral delivery to the brain. Typically the particles will be formulated in sterile saline or buffered solution for injection into the tissues or cells to be treated. The particles can be stored lyophilized in single use vials for rehydration immediately before use. Other means for rehydration and administration are known to those skilled in the art.

Optional pharmaceutically acceptable excipients include, but are not limited to, stabilizers and surfactants. Stabilizers are used to inhibit or retard decomposition reactions which include, by way of example, oxidative reactions.

The nanoparticles or nanoconjugates can be formulated in dosage unit form for ease of administration and uniformity of dosage. The expression "dosage unit form" as used herein refers to a physically discrete unit of conjugate appropriate for the patient to be treated. It will be understood, however, that the total daily usage of the compositions will be decided by the attending physician within the scope of sound medical judgment. For any nanoparticle or nanoconjugate, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index and it can be expressed as the ratio, LD50/ED50. Pharmaceutical compositions which exhibit large therapeutic indices are preferred. The data obtained from cell culture assays and animal studies can be used in formulating a range of dosages for human use.

II. Methods of Manufacture

A. Polymer Preparation

The polymers can be synthesized by any means known in the art. PEG or other coating agents can be conjugated to the core polymer using a variety of techniques known in the art depending on whether the coating is covalently or non-covalently associated with the particles.

In some embodiments the PEG or other coating agent can be covalently attached to the core polymer by reacting functional groups on the particles with reactive functional groups on the PEG or other coating agent to make a copolymer. For example, aminated PEG can be reacted with reactive functional groups on the particles, such as carboxylic acid groups, to covalently attach the agent via an amide bond.

In one embodiment methoxy-PEG-NHS is conjugated to 25 kDa branched PEI to yield a PEG-PEI copolymer. The extent of PEGylation of the resulting PEI copolymer can be varied by varying the molar ratio of PEG added to the PEI.

In some embodiments nanoparticles are formed of a mixture of PEGylated and non-PEGylated polymers. The non-PEGylated polymers can contribute a defined amount of the total free amines, such as 5%, 10%, 15%, 20%, 25%, 30%, 35%, 40%, 45%, 50% or more than 50% of the total free amines in the particles.

B. Nanoparticles

The disclosed nanoparticle gene carriers can be formed from one or more cationic polymers, one or more PEGs or other coating agents, and one or more nucleic acids using any suitable method for the formation of polymer nanoparticles known in the art. The methods employed for nanoparticle formation will depend on a variety of factors, including the characteristics of the polymers present in the nanoparticle gene carrier, as well as the desired particle size and size distribution.

In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing nanoparticles gene carriers include, but are not limited to, solvent evaporation, solvent removal, spray drying, phase inversion, low temperature casting, and nanoprecipitation. Suitable methods of particle formulation are briefly described below. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle gene carrier during particle formation.

1. Solvent Evaporation

In this method the polymer is dissolved in a volatile organic solvent, such as methylene chloride. Nucleic acid is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

2. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

3. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried.

4. Phase Inversion

Microspheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposomes).

III. Methods of Use

It has been established that the density and composition of a surface coating agent such as PEG can determine the ability of the particles to diffuse throughout the brain parenchyma. The diffusion limitations of nanoparticles (~50 nm diameter particles) was investigated ex vivo, in excised rodent brain slices, as described in the Examples. Using multiple particle tracking (MPT) and optimized PEGylation protocols, it was shown that differences in PEG coating density and molecular weight have a significant impact on shielding particles from adhesive interactions and enabling them to penetrate and distribute more uniformly in vivo.

Therefore, the particle compositions described herein can be used to administer one or more therapeutic, prophylactic, and/or diagnostic agents directly to the brain to treat one or more diseases or disorders of the brain.

A. Therapeutic Uses

Nanoparticle gene carriers carrying one or more nucleic acid can be utilized to deliver nucleic acid cargo for therapeutic or prophylactic purposes, such as in a method of gene therapy. Methods of gene therapy typically rely on the introduction into the cell of a nucleic acid molecule that alters the genotype of the cell. Introduction of the nucleic acid molecule can correct, replace, or otherwise alter the endogenous gene via genetic recombination. Methods can include introduction of an entire replacement copy of a defective gene, a heterologous gene, or a small nucleic acid molecule such as an oligonucleotide. For example, corrective gene can be introduced into a non-specific location within the host's genome. This approach typically requires delivery systems to introduce the replacement gene into the cell, such as genetically engineered viral vectors.

1. Disorders or Diseases to be Treated

Exemplary diseases and disorders of the brain that can be treated by the disclosed compositions and methods include neoplasms (cancers, tumors, growths), infections (HIV/AIDS, Tuberculosis), inflammation (multiple sclerosis, transverse myelitis and other autoimmune processes, cerebral or tissue edema and other reactive processes), acquired or degenerative conditions (Alzheimer's disease, Parkinson's disease, stroke, amylotrophic lateral sclerosis, acute and chronic traumatic and pain syndromes), congenital or genetic abnormalities (neurofibromatosis, mucopolysaccaridoses, tuberous sclerosis, Von Hippel Lindau), epigenetic conditions and brain trauma or injury.

B. Methods of Administration and Dosing

The disclosed nanoparticles can be administered by a variety of routes of administration. In certain embodiments the particles are administered directly to the brain. In other embodiments the particles are administered systemically.

The composition of the brain ECM, including the physico-chemical properties of its components and the space between them ('pores'), are key factors that determine the penetration of substances within the brain.

Unshielded, negatively charged particles with exposed hydrophobic regions have significantly hindered diffusion regardless of particle size. The hydrophobic interactions between particle surfaces and ECM components can be a source of significant adhesion. Adequate surface shielding from potential interactions, including electrostatic and hydrophobic forces, are crucial for rapid diffusion in the brain.

Mechanisms for the enhanced delivery of the disclosed gene vectors to the brain are disclosed. Enhanced local delivery can be achieved via convection, electricomagnetic, or other forces Enhanced systemic delivery can be achieved via co- or sequential administration with permeabliization agents such as but not limited to pharmacologic substances (e.g. cytokines), mechanical barrier disruption (e.g. ultrasound), or osmotic changes (e.g. mannitol). Other methods of delivery include intrathecal or intra-ventricular delivery via cerebro-spinal fluid spaces, intra-nasal administration or delivery via the olfactory bulb and systemic delivery via oral, intravenous, or intra-arterial administration.

1. Convection Enhanced Delivery

In some embodiments the brain penetrating capability of the disclosed nanoparticles is enhanced following convection enhanced delivery (CED). CED is a method in which drugs are delivered through a needle installed intraparenchymally into the brain and attached to a pump providing positive pressure and constant flow of the infusates. For example, densely PEGylated nanoparticles drugs can be delivered through one to several catheters placed stereotactically, for example, directly within a brain tumor mass or around the tumor or the resection cavity.

In some embodiments CED can significantly enhances distribution of varied-size molecules and increase the infused compounds' locoregional concentration. In certain embodiments the use of CED to deliver densely PEGylated particles enhances the distribution of the particles throughout the brain to an extent that is greater than expected. In some embodiments gene vector distribution and high-level transgene expression can be achieved throughout the entire striatum. CED is unlikely to provide a significant benefit if particles, such as the reference particles, remain entrapped in the brain parenchyma due to adhesive interactions and/or steric obstruction. Thus, physicochemical properties of particles that allow unhindered diffusion in the brain parenchyma remain critical for achieving enhanced particle penetration following the CED.

2. Administration Regimes

In general the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

Regardless of systemic, intrathecal, or local delivery into the brain parenchyma itself, penetration of bioactive or imaging agents in the brain and other tissues has been a key hurdle to effective therapy and diagnostics. Numerous studies using viral, nanoparticle, and convection-enhanced delivery have failed due to limited movement of substances within the brain. Therefore, defining the critical limiting parameters and designing strategies to enhance brain penetration will likely improve the efficacy of these treatments. Densely-PEGylated nanoparticles offer numerous additional advantages, including increased particle diffusion, improved stability, and prolonged sustained-release kinetics. These factors are known to correlate with the efficacy of many therapeutics and will likely have a significant impact on the utility of nano-sized carriers for diagnostic and therapeutic delivery to the brain.

EXAMPLES

The present invention will be further understood by reference to the following non-limiting examples.

Example 1: Preparation of Vectors to Shield the Positive Surface Charge Intrinsic to Cationic Polymer-Based Gene Vectors Materials and Methods
Polymer Preparation Methoxy PEG N-hydroxysuccinimide (mPEG-NHS, 5 kDa, Sigma-Aldrich, St. Louis, Mo.) was conjugated to 25 kDa branched polyethyleneimine (PEI) (Sigma-Aldrich, St. Louis, Mo.) to yield a PEG5k-PEI copolymer as previously described [30]. Briefly, PEI was dissolved in ultrapure distilled water, the pH was adjusted to 7.5-8.0 and mPEG-NHS was added to the PEI solution at various molar ratios and allowed to react overnight in 4° C. The polymer solution was extensively dialyzed (20,000 MWCO, Spectrum Laboratories, Inc., Rancho Dominguez, Calif.) against ultrapure distilled water and lyophilized. Nuclear magnetic resonance (NMR) was used to confirm a PEG:PEI ratio of 8, 26, 37 and 50. 1H NMR (500 MHz, D2O): δ 2.48-3.20 (br, CH2CH2NH), 3.62-3.72 (br, CH2CH2O). The poly-L-lysine 30-mer (PLL) and PEG5K-PLL block copolymers were synthesized and characterized as previously published [Suk, J. S., et al. *J Control Release*, 2014; Kim, A. J., et al., *J Control Release*, 2012. 158(1): p. 102-7.]. The lyophilized polymers were dissolved in ultrapure distilled water and pH was adjusted to ~6.5-7.

Gene Vector Complexation

The pd1GL3-RL plasmid DNA was a kind gift from Professor Alexander M. Klibanov (M.I.T) and pEGFP plasmid was purchased by Clontech Laboratories Inc. (Mountainview, Calif.). The plasmid DNA was propagated and purified as previously described [Suk, J. S., et al. *J Control Release*, 2014]. Mirus Label IT® Tracker™ Intracellular Nucleic Acid Localization Kit (Mirus Bio, Madison, Wis.) was used to fluorescently tag plasmid DNA with a Cy3 or Cy5 fluorophore. Gene vectors were formed by the dropwise addition of 10 volumes of labeled or non-labeled plasmid DNA (0.2 mg/ml) to 1 volume of a swirling polymer solution. PEI solutions were prepared at previously optimized nitrogen to phosphate (N/P) ratio of 6 and at PEG5k-PEI to PEI molar ratio of 3. For the formulation of free PEI and (PEG5k)8-PEI based gene vector controls, the PEI solutions were prepared at N/P ratio of 6 using 100% of free PEI or (PEG5k)8-PEI, respectively. For fluorescence imaging, Cy3- or Cy5-labeled DNA was used to assemble fluorescently labeled gene vectors. The plasmid/polymer solutions were incubated for 30 min at room temperature to form gene vectors. Gene vectors were washed twice with 3 volumes of ultrapure distilled water, and re-concentrated to 1 mg/ml using Amicon® Ultra Centrifugal Filters (100,000 MWCO, Millipore Corp., Billerica, Mass.) to remove free polymers. DNA concentration was determined via absorbance at 260 nm using a NanoDrop ND-1000 spectrophotometer (Nanodrop Technologies, Wilmington, Del.). PEG-PLL nanoparticles were similarly prepared at an N/P ratio of 2 as previously described [Suk, J. S., et al. J Control Release, 2014; Kim, A. J., et al., *J Control Release*, 2012. 158(1): p. 102-7; Boylan, N.J., et al., *Biomaterials*, 2012. 33(7): p. 2361-71.].

Physicochemical Characterization of Nanoparticles

Hydrodynamic diameter, ζ-potential and polydispersity were measured in 10 mM NaCl at pH 7.0 by dynamic light scattering and laser Doppler anemometry, respectively, using a Nanosizer ZS90 (Malvern Instruments, Southborough, Mass.). Gene vectors were imaged using transmission electron microscopy (TEM, Hitachi H7600, Japan) to determine their morphology and size.

Results

To effectively shield the positive surface charge intrinsic to cationic gene vectors, gene vectors using copolymers of multiple 5 kDa PEG molecules conjugated to PEI (PEG5k-PEI) were formulated with a range of PEG to PEI molar ratios. As previously reported, PEGylation of cationic polymers may have negative influences on DNA complexation due to reduction of available positive charges resulting from the PEG conjugation and additional steric hindrance imposed by grafted PEG chains [Petersen, H., et al., *Bioconjug Chem*, 2002. 13(4): p. 845-54]. Thus, the conventional DNA complexation method, using only highly PEGylated PEI copolymers, yields loose, unstable DNA nanoparticles which are not likely to retain their stability in biological specimens. In order to achieve compact and colloidally stable gene vectors, vectors were formulated with a blend of PEG5k-PEI and free PEI with 25% of amines deriving from free PEI, as described by Suk, J. S., et al. *J Control Release*, 2014. Using a fixed amount of free PEI, the compaction of DNA in ~50 nm particles was achieved using PEG5k-PEI copolymers with a wide range of PEG to PEI molar ratios (Table 2). The use of a copolymer with a PEG to PEI ratio of 26, which is substantially higher than conventionally used PEGylation ratios [Petersen, H., et al., *Bioconjug Chem*, 2002. 13(4): p. 845-54; Malek, et al., *J Drug Target*, 2008. 16(2): p. 124-39; Merkel, et al., *Biomaterials*, 2011. 32(21): p. 4936-42], is sufficient to form gene vectors with a near neutral ζ-potential (Table 1) and potentially allows for brain penetration (brain penetrating nanoparticle; BPN hereafter). In the subsequent studies the BPN was compared to similarly sized conventionally PEGylated nanoparticles (CPN), consisting of PEGylated PEI with a lower PEG to PEI ratio of 8 [Petersen, et al., *Bioconjug Chem*, 2002. 13(4): p. 845-54; Malek, et al., *Toxicol Appl Pharmacol*, 2009. 236(1): p. 97-108; Lutz, et al., *Methods Mol Biol*, 2008. 433: p. 141-58.], and un-PEGylated PEI nanoparticles (UPN). The physicochemical properties of BPN, CPN and UPN are summarized in Table 1. Of note, CPN possessed larger particle diameter and more positive surface charge compared to BPN, suggesting the looser compaction and/or inferior surface coating.

TABLE 1

Physicochemical properties and diffusivity of gene vectors in rodent cortical tissue.

|  | Hydrodynmc Diameter ± SEM (nm) | ζ-potential ± SEM (mV) | PDI | Hydrodynmc Diameter in ACSF | $MSD_{AQ}/MSD_{Brain}$ |
|---|---|---|---|---|---|
| UPN | 47 ± 2 | 26 ± 1.2 | 0.15 | 392 ± 8 | 6900 |
| CPN | 59 ± 1 | 9.3 ± 0.5 | 0.17 | 172 ± 2 | 930 |
| BPN | 43 ± 5 | 2.9 ± 0.3 | 0.19 | 50 ± 9 | 260 |

Size, ζ-potential and polydispersity (PDI) were measured by dynamic light scattering (DLS) in 10 mM NaCl at pH 7.0 and are presented as average of at least 3 measurements±standard error (SEM). Mean square displacement (MSD) at 1 sec was measured using multiple particle tracking (MPT) of fluorescently labeled gene vectors in rodent brain slice. NP diffusivity in aCSF was calculated using the Stokes-Einstein equation and the mean particle diameter. Hydrodynamic diameter in aCSF was measured by DLS following incubation in aCSF at 37° C. for 1 hour. UPN: un-PEGylated Nanoparticles, CPN: Conventionally PEGylated Nanoparticles, BPN: Brain Penetrating Nanoparticles.

TABLE 2

Physicochemical properties and diffusivity of PEI-based gene vectors in rodent cortical tissue.

|  | Hydrodynmic Diameter ± SEM (nm) | ζ-potential ± SEM (mV) | PDI |
|---|---|---|---|
| $(PEG_{5k})_8$-PEI | 55 ± 4 | 6.7 ± 0.7 | 0.17 |
| $(PEG_{5k})_{26}$-PEI | 43 ± 5 | 2.9 ± 0.3 | 0.19 |
| $(PEG_{5k})_{37}$-PEI | 44 ± 1 | 3.4 ± 0.5 | 0.17 |
| $(PEG_{5k})_{50}$-PEI | 48 ± 3 | 1.8 ± 0.8 | 0.14 |

Size, ζ-potential and polydispersity (PDI) were measured by dynamic light scattering (DLS) in 10 mM NaCl at pH 7.0 and are presented as average of at least 3 measurements±standard error (SEM).

Nanoparticle diffusion in the brain predominantly takes place through the narrow tortuous space between cells

[Sykova, E. and C. Nicholson, *Physiol Rev,* 2008. 88(4): p. 1277-340]. The ECM, the main component of the extracellular space, imposes an adhesive and steric barrier to the movement of nanoparticles through the brain parenchyma. Nonspecific electrostatic interactions with the abundant negative charges of the ECM hinder the diffusion of poorly shielded cationic polymer-based gene vectors [Zimmermann, et al., *Histochem Cell Biol,* 2008. 130(4): p. 635-53; Ruoslahti, *Glycobiology,* 1996. 6(5): p. 489-92], as shown with UPN and CPN in this study. Hence, rapid brain penetration of BPN is most likely attributed to the efficient shielding of this positive surface charge intrinsic to the cationic polymer-based gene vectors. Moreover, the dense surface PEG coating enabled by the blending technique allows BPN to retain their compact sub-100 nm size in physiological conditions (i.e. CSF) required to move through the ECM mesh pores without being hindered by steric obstruction. In comparison, the loose compaction, lack of stability and the tendency towards aggregation of conventionally PEGylated cationic particles, including CPN, does not allow for efficient penetration through the ECM which has pore sizes smaller than 200 nm [Nance, E. A., et al., *Sci Transl Med,* 2012. 4(149): p. 149ra119, MacKay, et al. *Brain Res,* 2005. 1035(2): p. 139-53]. These results, demonstrate the importance of designing gene vectors capable of overcoming both the adhesive interactions and steric hindrance imposed by the brain ECM.

Example 2: Gene Vector Particles are Stable Following Incubation in Physiological Environment Materials and Methods PEI nanoparticle stability was assessed by incubating nanoparticles in artificial cerebrospinal fluid (aCSF; Harvard Apparatus, Holliston, Mass.) at 37° C. and conducting dynamic light scattering every 30 mins for 24 hours. After 1 hour of incubation, a fraction of the nanoparticle solution was removed and imaged using TEM.

Results

To predict the particle stability of gene vectors following in vivo administration, the in vitro stability in artificial cerebrospinal fluid (aCSF) was characterized over time at 37° C. (FIG. 1). UPN aggregated immediately after adding in aCSF. In 1 hour, the hydrodynamic diameter increased 8.3-fold and in 7 hours, the polydispersity was larger than 0.5, indicating loss of colloidal stability. CPN increased in diameter by 3-fold following incubation in aCSF and remained stable over 24 hours. BPN, formulated by the blend approach, exhibited improved stability in aCSF compared to both UPN and CPN. BPN remained unchanged over the first 1 hour followed by a 2 fold increase in diameter which remained stable over 24 hours (Table 1; FIG. 1). These results were further confirmed by transmission electron micrographs of gene vectors in ultrapure water and after 1 hour incubation in aCSF at 37° C. Incubation of UPN in aCSF resulted in the formation of large aggregates. BPN and CPN qualitatively increased in size but retained their integrity.

Example 3: Gene Vector Particles are Non-Toxic In Vitro and In Vivo

Materials and Methods

Cell Culture

9 L gliosarcoma cells were provided by Dr. Henry Brem. 9 L immortalized cells were cultured in Dulbecco's modified Eagle's medium (DMEM, Invitrogen Corp., Carlsbad, Calif.) supplemented with 1% penicillin/streptomycin (pen/strep, Invitrogen Corp., Carlsbad, Calif.) and 10% heat inactivated fetal bovine serum (FBS, Invitrogen Corp., Carlsbad, Calif.). When cells were 70-80% confluent, they were reseeded in 96-well plates to assess toxicity and in 24-well plates to assess transfection and cell uptake of gene vectors. Rabbit primary astrocytes were provided by Dr. Sujatha Kannan. Mixed cell culture was prepared from day 1 neonatal rabbits and astrocytes were isolated using the conventional shake off method. Astrocytes were cultured in DMEM supplemented with 1% pen/strep and 10% FBS and passaged once; when cells were 70-80% confluent they were reseeded in 96-well plates for cell viability assay. Rat brain primary astrocytes were provided by Dr. Arun Venkatesan. Rat brain primary mixed cultures were isolated form neonatal P3-P6 rats and astrocytes were isolated with the conventional shake off method as previously published [Hosmane, et al., *Journal of Neuroscience,* 2012. 32(22): p. 7745-7757]. Cells were cultured in DMEM/F12 (Invitrogen Corp., Carlsbad, Calif.) supplemented with 10% FBS and 1% pen/strep. When cells were 70-80% confluent on passage one, they were immediately reseeded in 96-well plates to assess gene vector toxicity and in 24-well plates to assess transfection and cell uptake of gene vectors.

In Vitro Toxicity

Cells were seeded onto 96-well plates at an initial density of $1.0 \times 10^4$ cells/well and incubated at 37° C. After 24 h, cells were incubated with a wide range of doses of DNA nanoparticles in media for 24 h at 37° C. Cell viability was assessed using the Dojindo cell counting kit-8 (Dojindo Molecular Technologies, Inc., Rockville, Md.). Absorbance at 450 nm was measured spectrophotometrically using the Synergy Mx Multi-Mode Microplate Reader (Biotek, Instruments Inc.).

Results

Despite their wide use as non-viral gene vector systems, PEI-based gene vectors have raised concerns of their toxicity due to their high positive charge density [Petersen, et al., *Bioconjug Chem,* 2002. 13(4): p. 845-54; Merkel, et al., *Biomaterials,* 2011. 32(21): p. 4936-42]. To ensure their safety for administration to the CNS, the in vitro toxicity mediated by the gene vectors was thoroughly characterized in primary astrocytes derived from neonatal rabbits (FIG. 2A), primary astrocytes derived from rats (FIG. 2B) and 9 L rat gliosarcoma cells (FIG. 2C) using plasmid concentrations from 1 to 10 μg/ml. Both UPN and CPN exhibited cytotoxicity in all three cells tested; UPN resulted in 50% cell death at 5, 10, and 10 μg/ml of plasmid concentration for primary rabbit cells, primary rat cells and 9 L cells, respectively. Similarly, CPN resulted in less than 50% cell viability at 10 μg/ml for primary rabbit and primary rat astrocytes. CPN treatment of 9 L gliosarcoma cells at 5 and 10 μg/ml of plasmid resulted in approximately 70% cell viability.

Figures 2A, 2B, 2C, 2D:
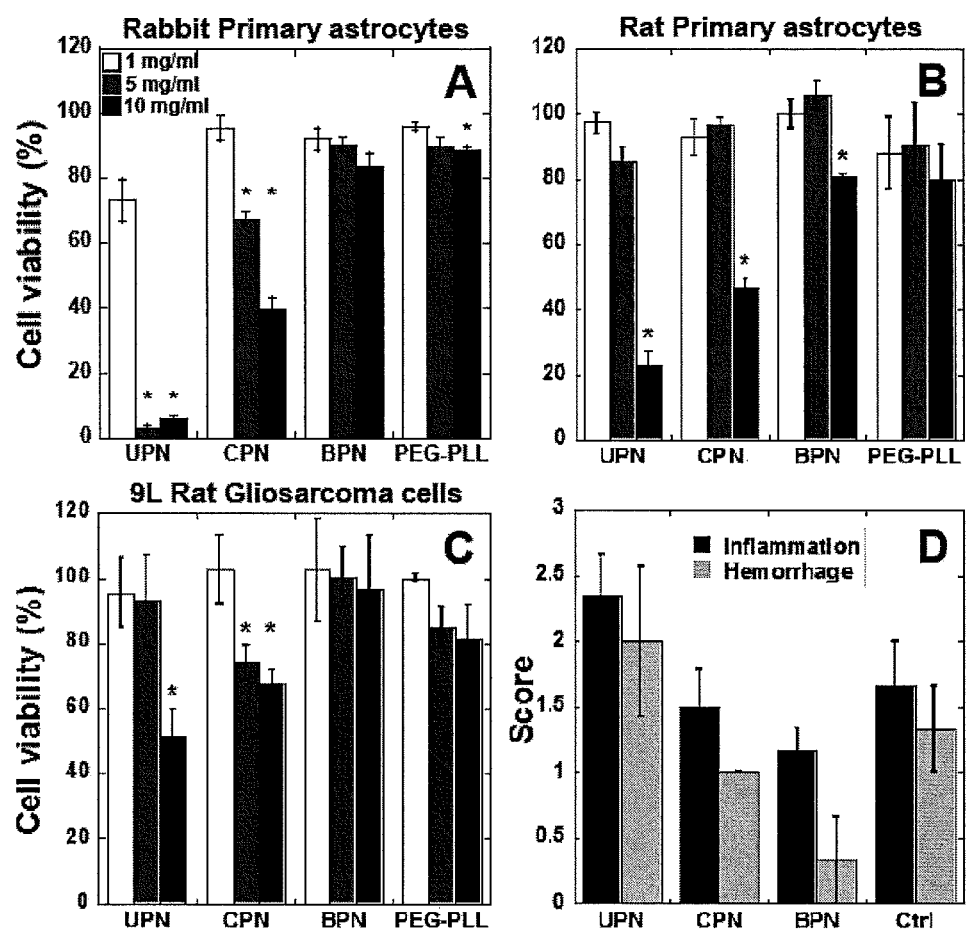
FIGS. 2A to 2D are bar graphs.

Contrary to these findings, the BPN were non-toxic in rabbit primary astrocytes and 9 L gliosarcoma cells and showed only mild toxicity in rat primary astrocytes even at a high concentration of 10 μg/ml (FIGS. 2A-2D). the toxicity of BPN was compared to a PEG-PLL nanoparticle system shown to be safe in animals [Yurek, et al., *Cell Transplant,* 2009. 18(10): 1183-1196; Yurek, et al., *Mol Ther,* 2009. 17(4): 641-650] and humans [Konstan, et al., *Hum Gene Ther,* 2004. 15(12): 1255-1269]. BPN and PEG-PLL exhibited similar safety profiles in all three cell types at varying concentrations. In summary, conventional PEG coating does not sufficiently reduce cytotoxicity [Davies, et al., *Mol Ther,* 2008. 16(7): 1283-1290]. However, BPN demonstrate favorable safety profiles even at high plasmid doses. The in vivo safety profile of these gene vectors were further histopathologically characterized, following CED. In accordance to these in vitro data, UPN demonstrated higher signs of toxicity than CPN and BPN. BPN and CPN demonstrated no toxicity as their effect did not differ from that of normal saline administration (FIG. 2D). Importantly, regardless of the gene vector type, inflammation and hemorrhage was confined around the injection site and did not propagate through the brain tissue.

Cytotoxicity of cationic polymer-based gene vectors has long been acknowledged as a limitation for the use of these versatile and potent gene delivery platforms [Petersen, et al., Bioconjug Chem, 2002. 13(4): 845-854; Merkel, et al., Biomaterials, 2011. 32(21): 4936-4942.]. In good agreement with previous observations [Petersen, et al., Bioconjug Chem, 2002. 13(4): 845-854; Davies, et al., Mol Ther, 2008. 16(7): 128312-90, Beyerle, et al., Toxicol Appl Pharmacol, 2010. 242(2): 146-154], conventional PEGylation (i.e. CPN) is not sufficient to significantly improve the in vitro safety profile of cationic polymer-based gene vectors. Dense PEGylation achieved by the blend approach drastically decreases the toxicity of BPN, leading to a favorable safety profile similar to the widely used PEG-PLL nanoparticle system shown to be safe in animals [Yurek, et al., Cell Transplant, 2009. 18(10): 1183-1196; Yurek, et al., Mol Ther, 2009. 17(4): 641-650] and humans [Konstan, et al., Hum Gene Ther, 2004. 15(12): 1255-1269.].

Example 4: PEGylated Nanoparticle Gene Vectors have High Uptake and Transfection Efficiencies Materials and Methods
In Vitro Transfection Cells were seeded onto 24-well plates at an initial density of $5.0 \times 10^4$ cells/well. After 24 h, cells were incubated with pd1GL3-RL plasmid in gene vector form (1 µg DNA/well) in media for 5 h at 37° C. Cationic polymer-based gene vector transfection was compared to free plasmid control. Subsequently, nanoparticles and culture media were replaced with fresh media. After additional 48 h of incubation at 37° C., media was removed and 0.5 ml of 1× Reporter Lysis Buffer was added. Cells were subjected to three freeze-and-thaw cycles to assure complete cell lysis, and supernatants were obtained by centrifugation. Luciferase activity in the supernatant was then measured using a standard luciferase assay kit (Promega, Madison, Wis.) and a 20/20 n luminometer (Turner Biosystems, Sunnyvale, Calif.). The relative light unit (RLU) was normalized to the total protein concentration of each well measured by Bio-Rad protein assay.

Results

Figures 3A, 3B, 3C, 3D:
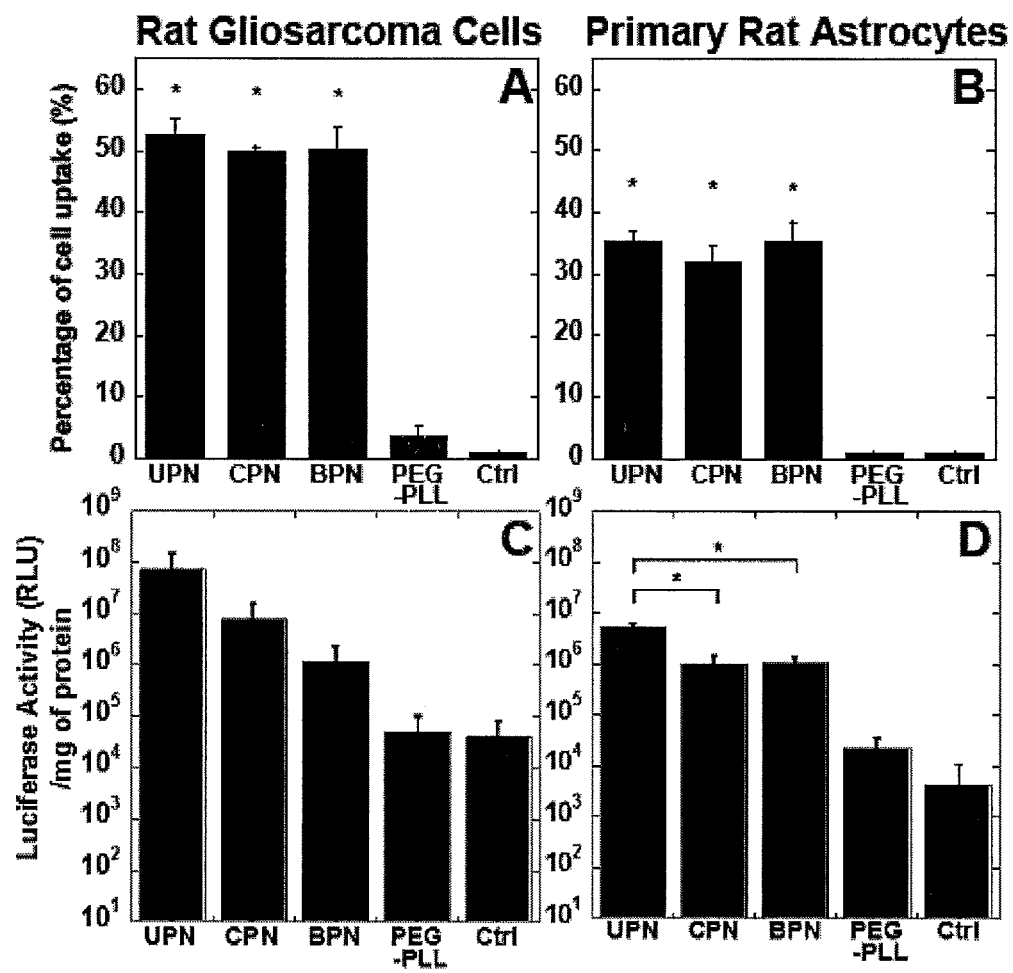
FIGS. 3A to 3D are bar graphs.

Cell uptake and transfection efficiencies of the gene vectors were characterized in vitro. PEG coating has been shown to reduce particle uptake by cells [Amoozgar, Z. and Y. Yeo, Wiley Interdiscip Rev Nanomed Nanobiotechnol, 2012. 4(2): 219-233; Hatakeyama, et al. Adv Drug Deliv Rev, 2011. 63(3): 152-160]. However, in good agreement with previous reports [Mishra, et al., Eur J Cell Biol, 2004. 83(3): 97-111.], conventional PEGylation did not affect cell uptake by PEI-based gene vectors (i.e. CPN). The small particle size may contribute to effective uptake of PEGylated nanoparticles [Pamujula, et al., J Pharm Pharmacol, 2012. 64(1): 61-67; Hu, Y., et al., J Control Release, 2007. 118(1): 7-17]. BPN, despite their denser PEG coating compared to CPN, also presented no difference in uptake compared to UPN and CPN. All three PEI-based gene vectors were detected in 50% of 9 L immortalized cells (FIG. 3A) and 35% of rodent primary cells (FIG. 3B). The uptake of these gene vectors was ~17 and ~35 fold higher than clinically tested PEG-PLL gene vectors in 9 L immortalized and primary astrocytes, respectively (p<0.05). This difference translated to a significantly higher luciferase expression by PEI-vector treated cells in comparison to cell treated with PEG-PLL vector at the same plasmid dose. Despite the similar cell uptake among different PEI-based gene vectors, significantly lower in vitro transgene expression by both CPN and BPN was found compared to UPN (FIGS. 3C and 3D), in accordance with previous observations [Mishra, et al., Eur J Cell Biol, 2004. 83(3): 97-111].

Example 5: BPN PEGylated Nanoparticle Gene Vectors have Rapidly Penetrate the Brain Parenchyma Materials and Methods
Animal Studies Female Fischer 344 rats, weighing 120-140 g each, were purchased from Harlan Laboratories (Frederick, Md.). The use of inbred rats was preferred to other outbred strains due to the radical impact of genetic differences in gene expression [Liu, et al., J Biol Chem, 2002. 277(7): 4966-4972]. They were housed in standard facilities and given free access to food and water. All animals were treated in accordance with the policies and guidelines of the Johns Hopkins University Animal Care and Use Committee. All surgical procedures were performed using standard, sterile surgical technique.

Rats were anesthetized with a mixture of ketamine-xylazine as previously described [Recinos, et al., Neurosurgery, 2010. 66(3): 530-537; discussion 537]. Briefly, 350 µL of a ketamine (75 mg/kg), xylazine (7.5 mg/kg), ethanol (14.25%), and 0.9% normal saline solution was administered intraperitoneally. A midline scalp incision was made to expose the coronal and sagittal sutures and a burr whole was drilled 3 mm lateral to the saggital suture and 0.5 mm posterior to the bregma. Following the administration of nanoparticle solution the skin was closed using biodegradable sutures (POLYSORB™ Braided Absorbable Sutures 5-0) and Bacitracin was applied.

To study the diffusion based spread of nanoparticles in vivo, N=3 animals were used; a 33 gauge 10 µl Hamilton Neuro Syringe mounted to a stereotaxic headframe was lowered to a depth of 3.5 mm and retracted 1 mm to create a pocket in the rodent striatum in order to minimize the convective flow during infusion. A 10 µl solution of Cy5 labeled conventionally PEGylated nanoparticles and Cy3 labeled brain penetrating nanoparticles at a plasmid concentration of 500 µg/ml per particle type was administered as a bolus injection at 2 µl/min Animals were sacrificed 2 hours following the injection.

To study the distribution of PEI based gene vectors following convection enhanced delivery in the rodent striatum N=6 rats were used; A 33 gauge 50 µl Hamilton Neuro Syringe mounted to a stereotaxic headframe was lowered to a depth of 3.5 mm. A 20 µl solution of Cy3 labeled CPNs and Cy5 labeled BPNs at a plasmid concentration of 500 µg/ml per particle type in normal saline was administered. The rate of infusion was set at 0.33 µl/min, using a Chemyx Inc. Nanojet Stereotaxic syringe pump (Chemyx, Stafford, Tex.). Animals were sacrificed 5 hours following the injection. To examine the dependence of distribution on nanoparticle concentration co-injections were also performed at half the plasmid concentration, 250 µg/ml per particle type, in normal saline.

To assess the distribution of transgene expression following CED administration of gene vectors, at least N=4 rats per particle type were used; Plasmid encoding fluorescent eGFP reporter protein with a cytomegalovirus (CMV) promoter was complexed into the various PEI-based nanoparticle formulations and infused in a 20 µl solution of 1 mg/ml plasmid solution using the same parameters described above. Animals were sacrificed 48 hours following CED administration and harvested brains were fixed in 4% formaldehyde.

For Western blot analysis of in vivo transfection following CED of gene vectors, N=3 rats per particle type were used and the exact same experimental procedures followed for imaging based analysis of distribution of transfection were used. Animals were sacrificed 48 hours following CED administration and immediately placed on ice and a 4 mm thick coronal slice of the striatum from −2 mm to 2 mm from the injection site was dissected and stored in −80° C. for Western blot analysis.

To assess the safety profile of the gene vectors in vivo following CED administration, N=3 rats per group were used. Various PEI-based formulations were infused in in a 20 µl solution at a 1 mg/ml plasmid concentration as described above. A normal saline solution was infused as a negative control for comparison. Animals were sacrificed 4 days following administration and the harvested brains were fixed in 4% formaldehyde, processed, sectioned and stained with hematoxylin and eosin. Blind histopathological analysis was performed by a board certified neuropathologist and tissues were scored from 0-3 for indications of inflammation and hemorrhage (0: no inflammation/hemorrhage, 1: mild, 2: moderate, 3: severe).

Multiple Particle Tracking in Rodent Brain Slices

Multiple particle tracking (MPT) was used to estimate the mean square displacement (MSD) of fluorescent gene vectors in ex vivo rodent brain slices as previously published [Nance, et al., *Sci Transl Med*, 2012. 4(149): 149ra119]. Briefly, brain was harvested from adult Fisher rats and incubated in aCSF for 10 minutes on ice. Brain was sliced into 1.5 mm coronal slices using a Zivic brain matrix slicer (Zivic Instruments, Pittsburgh, Pa.) and placed on custom made slides. Half a microliter of fluorescently labeled gene vectors was injected on the cerebral cortex at a depth of 1 mm using a 50 µl Hamilton Neuro Syringe (Hamilton, Reno, Nev.) mounted on a stereotaxic frame. Tissues were covered by a 22 mm×22 mm coverslip to reduce tissue movement and bulk flow. Particle trajectories were recorded over 20 seconds at an exposure time of 66.7 ms by a Evolve 512 EMCCD camera (Photometrics, Tucson, Ariz.) mounted on an inverted epifluorescence microscope (Axio Observer D1, Zeiss; Thornwood, N.Y.) equipped with a 100×/1.46 NA oil-immersion objective. Movies were analyzed with a custom made MATLAB code to extract x, y-coordinates of gene vectors centroids over time and calculate the mean square displacement of each particle as a function of time [Nance, et al., *Sci Transl Med*, 2012. 4(149): p. 149ra119; Schuster, et al., *Biomaterials*, 2013. 34(13): p. 3439-46]. The spatial resolution to the noise to signal ratio correlation was estimated using immobilized gene vectors on a glass slide [Martin, et al., *Biophys J*, 2002. 83(4): 2109-17; Savin, et al., *Biophys J*, 2005. 88(1): 623-38]. Based on that correlation the average resolution of the MPT experiments was estimated to be ~0.009 µm$^2$ at 1 second. At least N=3 rat brains were used per gene vector type and at least 500 gene vectors were tracked per sample. The geometric mean of the MSDs for all nanoparticles was calculated per sample and the average of different rodent brains was calculated as a function of time. Histograms were generated from the MSD of every nanoparticle at a time scale of τ=1 sec. Theoretical MSD of nanoparticles in ACSF was calculated using Stokes-Einstein equation and the mean particle diameter calculated through dynamic light scattering.

Imaging and Analysis

Freshly harvested brains were fixed in 4% formaldehyde overnight followed by gradient sucrose solution processing before cryosection. Tissues were sectioned coronally into 100 micrometer thick slices using Leica CM 1905 cryostat. Slices were stained with DAPI (Molecular Probes, Eugene, Oreg.) and imaged for DAPI (cell nuclei), Cy3 and Cy5 or Alexa Fluor 488 (eGFP) using confocal LSM 710 microscope under 5× and 10× magnification (Carl Zeiss; Hertfordshire, UK). Settings were carefully optimized to avoid background fluorescence based on non-injected control rat brains. Laser power, pinhole, gain, offset and digital gain were selected separately for each magnification and kept constant throughout the study.

Statistical Analysis

Statistically significant differences between two groups were analyzed with a two-tailed Student's t test assuming unequal variances or paired student's t test when allowed. Multiple comparisons were performed using one-way analysis of variance (ANOVA) followed by post hoc test using SPSS 18.0 software (SPSS Inc. Chicago, Ill.).

Results

Figures 4A, 4B, 4C:
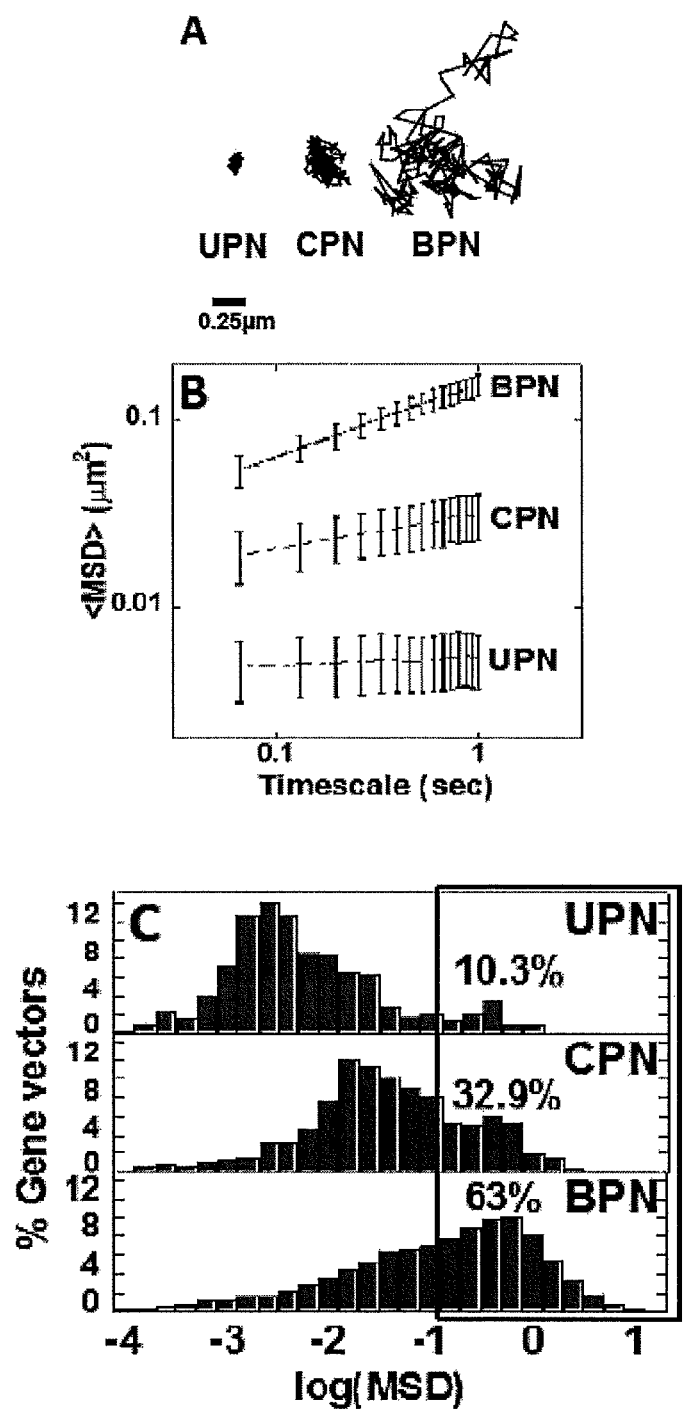
FIG. 4A shows trajectories of UPN, CPN and BPN nanoparticles over 20 seconds, at a time scale of 1 second. The scale bar represents 0.25 µm.
FIG. 4B is a graph showing ensemble-averaged geometric mean of mean square displacements (MSDs) of PEI based gene vectors (UPN, CPN and BPN) as a function of time (seconds). Data represent the ensemble average of at least three independent experiments, with N≥500 particles tracked for each experiment.
FIG. 4C is a panel of histograms showing % of gene vectors over log mean square displacements (MSD) for each respective gene vector (UPN, CPN and BPN) from at least three independent experiments at a timescale of τ=1 sec.

The diffusion of BPN, CPN and UPN in the brain parenchyma was investigated. Due to their positive surface charge, the UPN were strongly hindered with constrained non-Brownian time-lapse traces. Similarly, CPN exhibited less constrained but still hindered non-Brownian motions. In contrast, BPN trajectories spanned over greater distances indicating the unhindered diffusion in brain tissue (FIG. 4A). Based on the trajectories, the ensemble averaged MSD (<MSD>) over 1 second was calculated; BPN presented <MSD>5- and 29-fold higher than CPN and UPN, respectively (FIG. 4B). The diffusion rates of UPN and CPN in brain tissue were 6,900- and 930-fold slower than their theoretical diffusion rates in aCSF, respectively, while BPNs moved only 260-fold slower in brain than in aCSF (Table 1). The individual particle data was represented in a histogram of logarithmic MSD (log 10MSD) of individual gene vectors. The distribution was largely unimodal for UPN and BPN; the majority of UPN displayed low MSD values and most of the BPN showed MSD that allowed rapid penetration in brain tissue. CPN were largely trapped but a minor population was able to rapidly penetrate the brain parenchyma (FIG. 4C). Defining rapidly moving nanoparticles as nanoparticles with log 10MSD≥−1, 10.3%, 32.9% and 63% of UPN, CPN and BPN, respectively, were able to move in the brain parenchyma.

To test whether the enhanced brain penetration ex vivo by the BPN translated to wide spread of these vectors in brain parenchyma in vivo, a bolus co-injection of fluorescently labeled CPN and BPN was performed in the rodent striatum. Following the administration, CPN only moderately escaped from the injection site 2 hours after the administration, whereas BPN homogeneously diffused farther away from the injection site covering a distance of approximately 300 µm.

The high transfection and subsequent expression of therapeutic proteins away from the point of administration, constitutes the cornerstone for efficacious gene delivery-based treatment of CNS diseases. Effectively coating cationic polymer-based gene vectors allows for transgene expression over a larger volume of the brain striatum.

However, PEGylation as a stealth coating strategy has been shown to decrease uptake, endosome escape and subsequent transgene expression [Amoozgar, et al., *Wiley Interdiscip Rev Nanomed Nanobiotechnol*, 2012. 4(2): 219-33; Hatakeyama, et al., *Adv Drug Deliv Rev*, 2011. 63(3): 152-60]. PEGylation of cationic polymer based gene vectors does not decrease cell entry, likely due to the small particle size, as suggested in previous reports [Pamujula, et al., *J Pharm Pharmacol*, 2012. 64(1): 61-7; Hu, et al., *J Control Release*, 2007. 118(1): 7-17], but leads to significantly lower transfection efficacy in vitro [Mishra, et al., *Eur J Cell Biol*, 2004. 83(3): 97-111; Ogris, et al., *AAPS PharmSci*, 2001. 3(3): E21]. This may be explained by the increased intracellular stability of BPN that may hinder the DNA unpackaging and the conjugation of PEG to primary amines that reduces buffering capacity of gene vectors and the subsequent endosome escape [Mishra, et al., *Eur J Cell Biol*, 2004. 83(3): 97-111; Sonawane, et al., *J Biol Chem*, 2003. 278(45): 44826-31].

Example 6: CED Acts with Gene Vector Physicochemical Properties to Enhance Distribution and Transgene Delivery of Dencely PEGylated Gene Vectors Materials and Methods
Imaging and Analysis The nanoparticle volume of distribution following CED administration was quantified by using a custom MATLAB script that subtracted the background fluorescence and thresholded the fluorescent intensities at 10% of the maximum intensity. Nanoparticle fluorescence in the corpus callosum due to backflow was excluded from quantification. Every 100 μm slice within 2 mm of the injection plane was imaged. The area of distribution on each slice was summated to calculate the total volume of nanoparticle distribution. The same process was followed for the analysis of the distribution of transgene expression mediated by PEI based gene vectors encoding for eGFP.

Antibodies and Western Blotting

For western blot analysis of in vivo transfection following CED, the antibodies used included anti-GFP (B-2): sc-9996 and anti-β-actin:sc-47778 (Santa Cruz Biotechnology, Santa Cruz, Calif.). Brain tissues were lysed using brief sonication in ice PBS buffer (1 mM PMSF, and 1 μg/ml each of aprotinin, leupeptin, and pepstatin A). Sampling buffer (10% glycerol, 2% SDS, 62.5 mM Tris-HCl, 2% β-mercaptoethanol, pH 6.8) was added and samples were boiled at 100° C. for 10 min. Samples were resorved by SDS—polyacrylamide gel electrophoresis (PAGE) and and proteins on gels were transferred to nitrocellulose (Bio-Rad, Hercules, Calif.) using a semidry blotter (Bio-Rad, Hercules, Calif.). The membrane was blocked with 3% BSA in TBST (10 mM Tris-Cl, pH 8.0, 150 mM NaCl, 0.5% TWEEN-20) and incubated overnight at 4° C. with primary antibodies Immunoblots were visualized by enhanced chemiluminescence method. Quantification of western blot results was performed using the Multi Gauge program (Fujifilm, Tokyo, Japan) [Elliott, et al., *Mol Biol Cell*, 2005. 16(2): 891-901].

Results

Figure 5A:
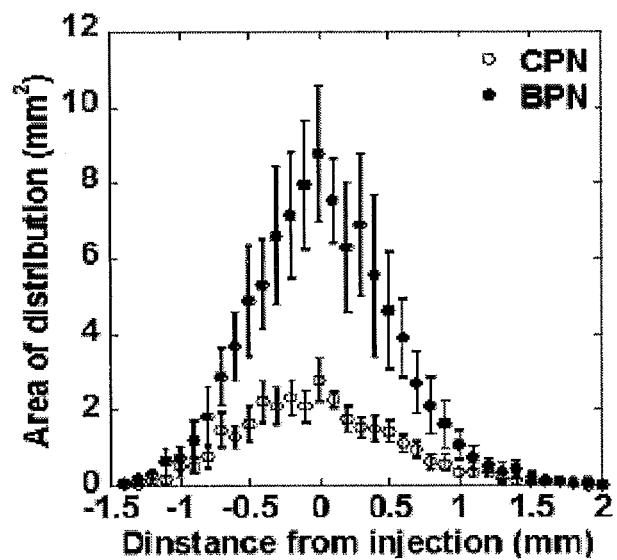
FIG. 5A is a graph showing image based Matlab quantification of area of distribution of PEI-based nanoparticles (mm$^2$) as a function of distance (mm) from the injection site, for CPN (○) and BPN (●) (N=6).
Figure 5B:
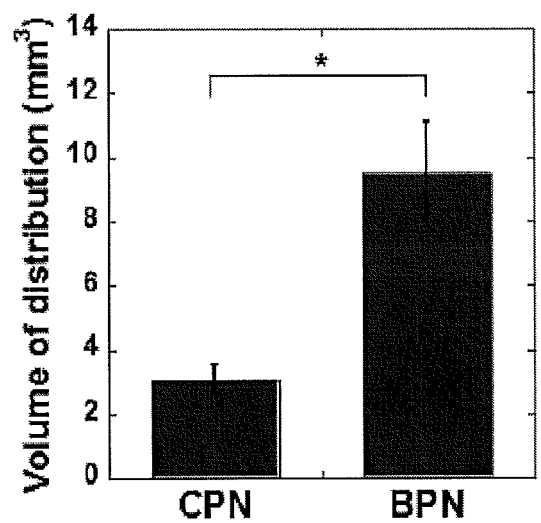
FIG. 5B is a histogram showing the volume of distribution (mm$^3$) of CPN and BPN gene vectors. * Denotes statistical significance P<0.05.
Figure 21:
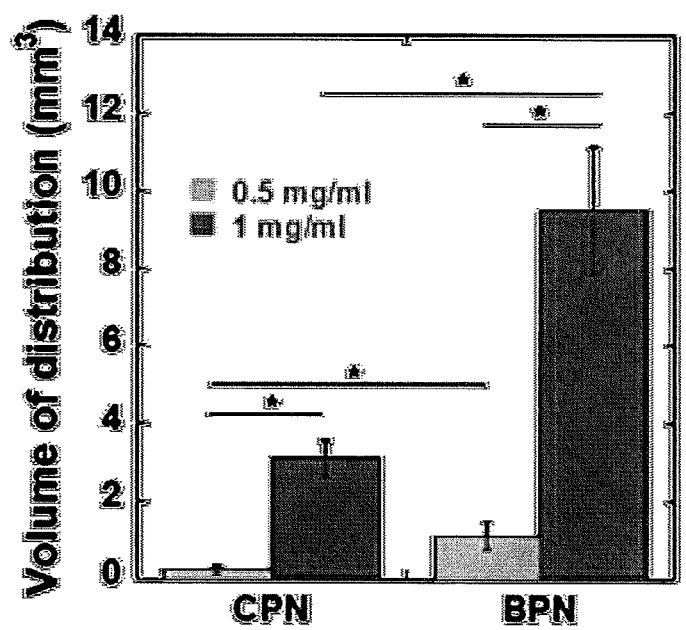
FIG. 21 is a bar graph demonstrating the volume of distribution (mm$^3$) of PEI CPN and BPN at plasmid concentrations of 0.5 mg/mL and 1 mg/mL. Data are taken from six independent experiments. * Denotes statistical significance of p<0.05.

Whether the dense PEG coating of BPN contributes to improved distribution following CED was assessed. To directly compare the spatial distribution of the gene vectors with different brain penetrating capacities following CED, Cy5-labeled BPN and Cy3-labeled CPN were co-infused. Densely PEGylated BPN homogeneously covered the rodent striatum, whereas less coated CPN were confined in the injection site. Within the coronal plane of injection, BPN covered a 3-fold larger area than CPN did (FIG. 5A) and the difference in distribution was statistically significant (p<0.05). Moreover, the overall volume of distribution of BPN was calculated to be 3.1-fold higher than for CPN (FIG. 5B). The concentration of nanoparticles in the CED infusate has been shown to have a significant effect on the volume of distribution [MacKay, et al. *Brain Res*, 2005. 1035(2): 139-53]. Indeed, co-infusing gene vectors at half the concentration resulted in 13- and 8-fold lower volume of distribution of CPN and BPN, respectively. Even at low plasmid concentrations BPN resulted in 4.6 fold higher volume of distribution in comparison to CPN (FIG. 21).

Figure 6A:
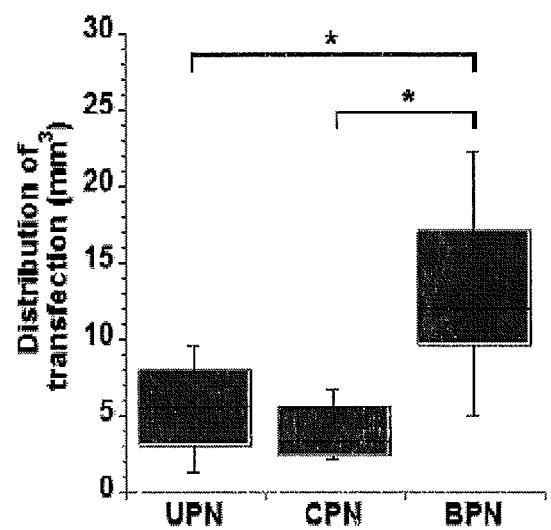
FIGS. 6A and 6B are a box graph (FIG. 6A) and a histogram (FIG. 6B), respectively, showing image based Matlab quantification of volume of distribution of eGFP expression (mm$^3$) for each of UPN, CPN and BPN gene vectors. (N=4-6). Data represents the mean±SEM. *Denotes statistical significance P<0.05.
Figure 6B:
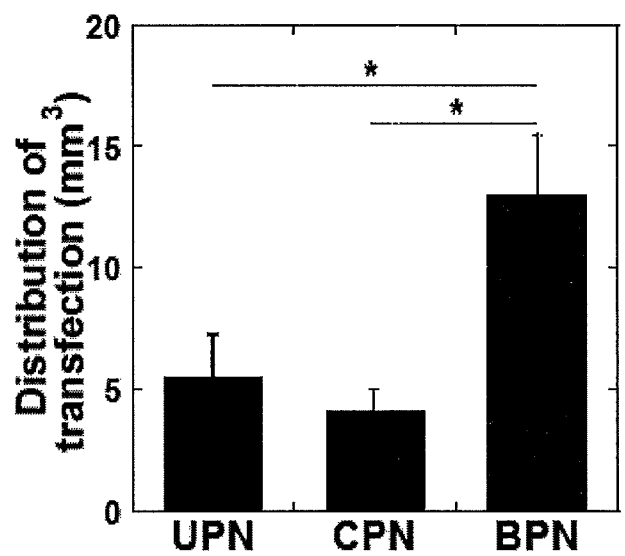
Figure 7:
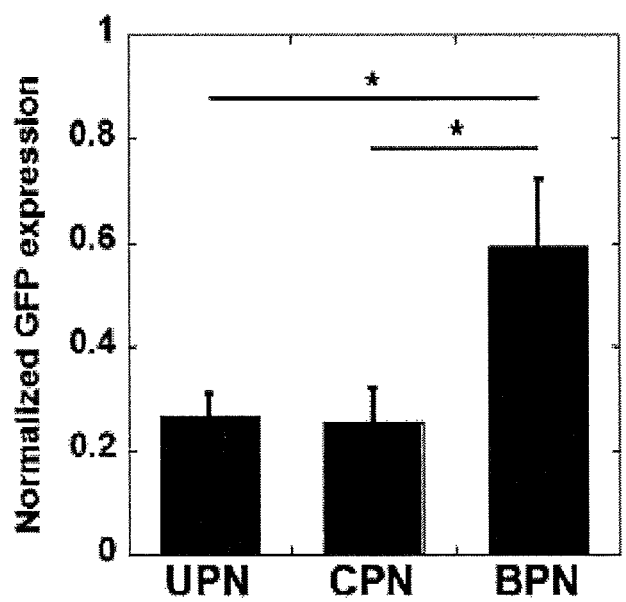
FIG. 7 is a histogram showing normalized GFP expression by UPN, CPN and BPN nanoparticle gene vectors in rodent striatum following CED administration. The expression level of GFP was normalized with β-actin. Data represents the mean±SEM. * Denotes statistical significance P<0.05.
Figure 8:
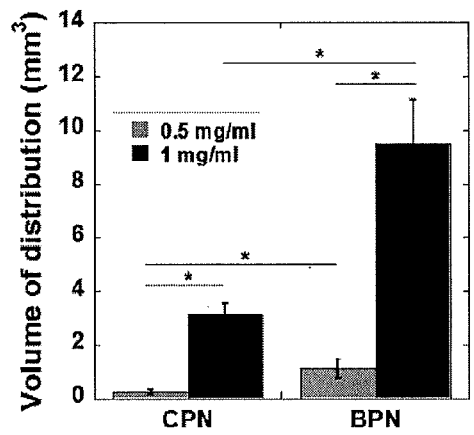
FIG. 8 is a histogram showing volume of distribution (mm$^3$) for CPN and BPN following CED at a concentration of 0.5 mg/ml and 1 mg/ml, respectively. *p<0.05.

Given the larger area of distribution of BPN and their ability to reach cells at further distances from the point of administration, the distribution of transfected cells following CED administration of gene vectors carrying plasmid DNA encoding eGFP was assessed. UPN and CPN treated animals demonstrated significant GFP expression surrounding the injection site and perivascular spaces. In contrast, BPN resulted in widespread transfection throughout the rodent striatum, which correlated well with the gene vector distribution analysis (FIGS. 5A-5B). In particular, BPN resulted in a statistically significant (p>0.05) difference in the GFP transgene expression with a 2.4- and 3.2-fold higher volume of transfection compared to CPN and UPN, respectively (FIGS. 6A and 6B). Absolute transgene GFP expression mediated by CED of UPN, CPN and BPN was quantitatively determined using Western blot analysis. BPN demonstrated a statistically significant, 2-fold higher overall transgene expression in the striatum in comparison to CPN and UPN (FIG. 7).

In contrast to the in vitro results, CED administration of BPN resulted in double the total amount of in vivo transgene expression in comparison to UPN and CPN, suggesting that the ability of BPN to transfect cells over a large area of the striatum may offset and even surpass their inferior intracellular delivery capacity The unhindered diffusion of BPN in the brain parenchyma translates to widespread distribution when administered using CED. It should be noted that a high density surface-shielding is required to achieve a CED-facilitated distribution of gene vectors; the insufficiently shielded CPN were unable to escape the injection site, and failed to mediate an enhanced distribution in transgene expression compared to unshielded UPN following CED.

Example 7: Synthesis of Nanoparticles Containing Poly L-Lysine and Branched PEG

Materials and Methods
Synthesis of Branched PEG (BrPEG)

BrPEG was synthesized in a two-step reaction. Diethylenetriaminepentaacetic acid (DTPA) anhydride was first conjugated to azido-trioxaundecanin at a 1:1 molar ratio in the presence of 2 molar equivalents of N, N-Diisopropylethylamine. The azido-DTPA resulting from this reaction was then conjugated with 4 molar equivalents of 5 kDa methoxy-PEG-amine (Creative PEGWorks, Winston Salem, N.C.) in the presence of 40, 5 and 3 molar equivalents of 1-Ethyl-3-(3-methylaminopropyl)carbodiimide (EDC), N-hydroxysuccinimide (NHS) and 4-dimethylaminopyridine (DMAP), respectively, in dimethylformamide (DMF). The reaction was carried out for 48 hours at 37° C. with constant stirring. For purification reaction products were dialyzed (6-8 kDa MWCO, Spectrum Laboratories, Inc., Rancho Dominguez, Calif.) against ultrapure water for 24 hours PEGylation of Poly-L-Lysine Poly-L-lysine (PLL) 30-mers with functionalized alkyne end groups and bromide counterions were used (Alamanda Polymers Inc., Huntsville, Ala.). For formation of linear PEGylated PLL polymers, PLL peptides were reacted with PEG (~5 kDa) (Creative PEGWorks, Winston Salem, N.C.) or branched PEG (~15 kDa) with functionalized azide groups at a molar ratio of 1:1. The click chemistry reaction was carried out at 37° C. for 48 hours in the presence of 0.1 molar equivalents of copper acetate, 5 molar equivalents of sodium ascorbate and Tris(benzyltriazolylmethyl)amine (TBTA) in 100 mM Tris buffer (pH 7.5). Reaction products, PLL-PEG (di-block of PLL and linear PEG) and PLL-BrPEG (di-block of PLL and branched PEG), were dialyzed against ultrapure water for 24 hours.

Purification of PEGylated Peptides and Exchange of Counter-Ions

Reaction products from PEGylation reactions were purified using size exclusion chromatography with SEPHADEX G15 (MWCO 1500, GE healthcare, Pittsburgh, Pa.) as the stationary phase and 50 mM ammonium acetate buffer (pH 7.4) as the mobile phase. During this process bromide counter-ions were exchanged with acetate counter-ions. Peptide concentrations in different fractions were monitored by measuring the absorbance at 220 nm (NANODROP ND-1000 spectrophotometer, NANODROP Technologies, Wilmington, Del.). High-molecular weight fractions containing peptide were pooled and dialyzed. Dialysis was carried out using dialysis tubes with a MWCO of 500 Da, against 2 liters of ultrapure water which was intermittently changed over the course of 24 hours. Purified products were lyophilized and stored at −80° C. until further use.

Particle Formulation

Gene vectors that mimicked the conventionally PEGylated Copernicus formulation (PLL-PEG) were formulated at a nitrogen (contributed by PLL) to phosphorus (contributed by DNA) ratio of 2. To determine the most suitable formulation parameters for compacting DNA in densely PEGylated gene vectors, nitrogen to phosphorus (N/P) ratios of 2 and 5 were tested using different ratios of PLL-BrPEG and PLL polymers. Gene vectors were complexed using 100% PLL-BrPEG (BR 100), a mixture of either 90% PLL-BrPEG and 10% PLL (BR 90) or 50% PLL-BrPEG and 50% PLL (BR 50). Gene vectors were formed by the drop-wise addition of 10 volumes of plasmid DNA (0.2 mg/ml) to 1 volume of polymer solution while vortexing at a slow speed. The plasmid/polymer solutions were incubated for 30 min at room temperature. Syringe filtration (0.2 μm) was used for removal of aggregates followed by removal of free polymer and collection of gene vectors at desired concentration by AMICON® Ultra Centrifugal Filters (100,000 MWCO, Millipore Corp., Billerica, Mass.).

DNA concentration was determined via absorbance at 260 nm using a NANODROP ND-1000 spectrophotometer (Nanodrop Technologies, Wilmington, Del.).

Results

Polymer Synthesis

Figure 9:
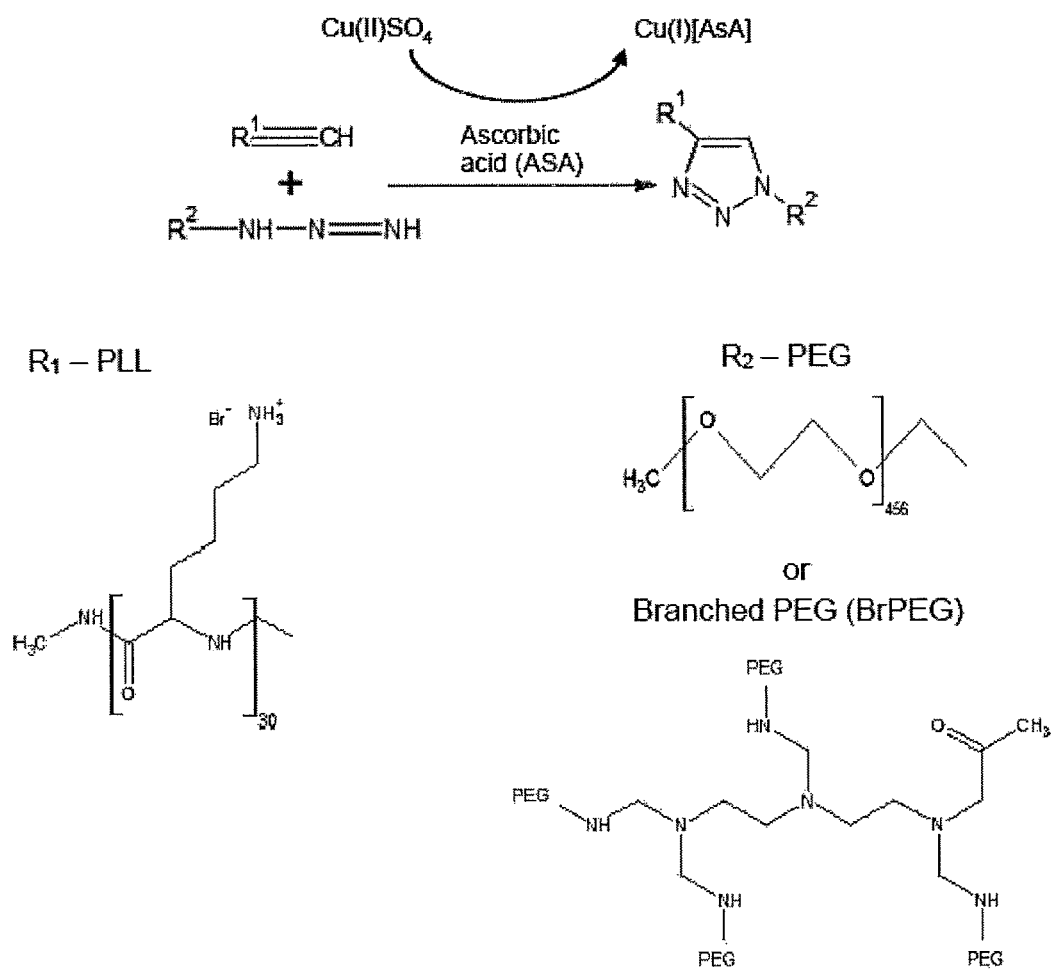
FIG. 9 is a schematic showing the click chemistry reaction for synthesis of PEGylated PLL polymers containing branched and unbranched PEG.

Branched PEG (BrPEG) was synthesized and analyzed by $^1$H-NMR to determine the ratio of PEG to DTPA. The results of the NMR indicated that an average of 3.65 PEG molecules were attached to each DTPA molecule. PLL-PEG and PLL-BrPEG polymers were synthesized as described in the materials and methods through click chemistry reactions (FIG. 9). The $^1$H-NMR spectra for polymers was used to determine the degree of PEGylation. The ratio of PEG to peptide was calculated based on the expected chemical shift contributed by protons attached to individual atoms. In the lysine monomer of PLL, the intensity contributed at a particular chemical shift by protons attached to each carbon are in the following ratio a:b:c:d:e=1:2:2:2:2. For carbons b and d, the corresponding peaks were too close to be clearly distinguished and thus were considered as a single peak. Since each lysine monomer was repeated 30 times, the peaks for a, c, b+d and e would represent 30, 60, 120 and 60 protons each. When keeping these as reference peaks each PEG molecule would be expected to contribute 456 protons since each repeating unit in PEG has 4 protons and 5 kDa PEG contains 114 repeating units. Thus the resultant products revealed a calculated PEG to peptide ratio of 1.12 for PLL-PEG and 3.16 for PLL-BrPEG polymers. Based on the NMR spectra both PEGylated peptides were deemed suitable for particle formulation with the degree of PEGylation for the densely PEGylated polymer being approximately 3.1 fold of the conventionally PEGylated polymer.

Particle Characterization

Figure 10:
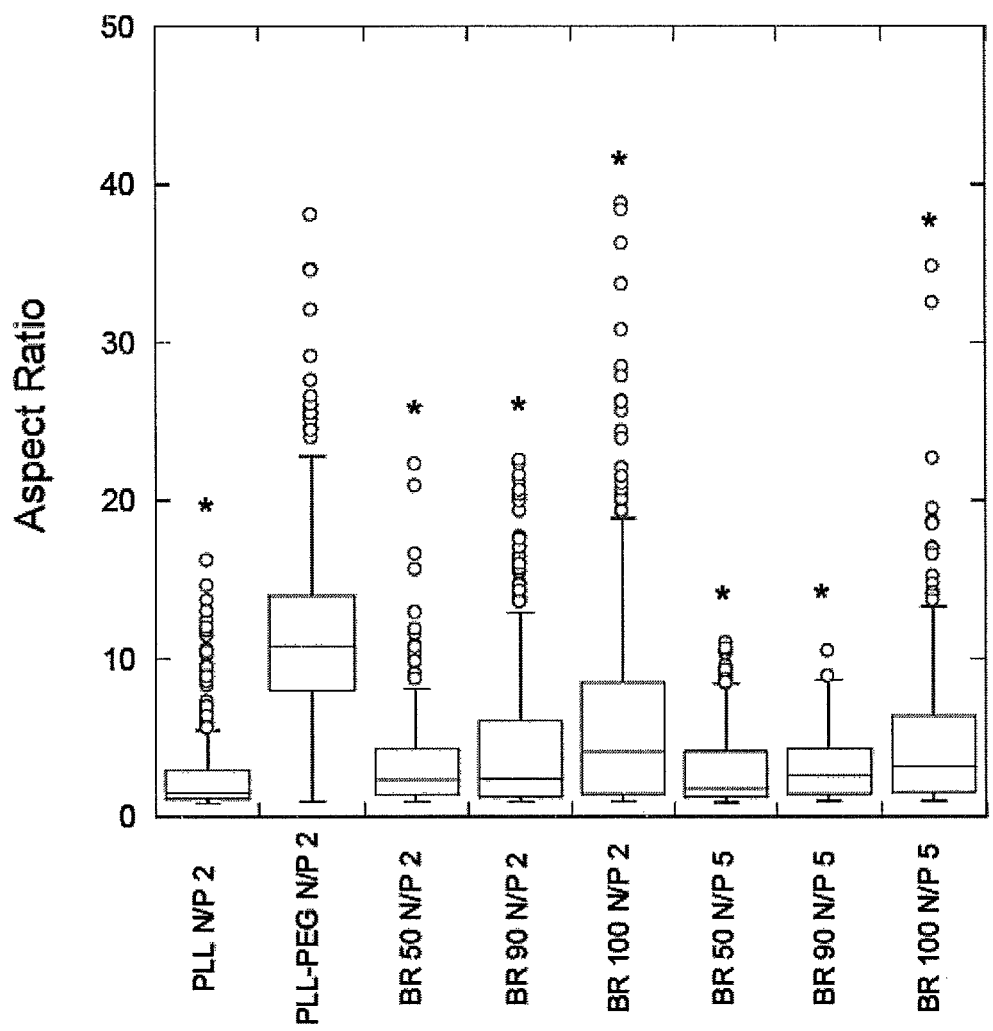
FIG. 10 is a graph showing the aspect ratio (major diameter/minor diameter) of nanoparticles formed from Poly L-lysine (PLL), PEG, or different percentages of Poly L-lysine and branched PEG (BR 50, BR 90 or BR 100) with nitrogen (polymer) to phosphorous (nucleic acid) (N/P) ratios of 2 or 5, respectively. * Denotes statistical significance in differences with PLL-PEG gene vectors, p value<0.05.

A comparison of TEM images revealed that conventional PLL-PEG gene vectors were rod shaped while both un-PEGylated PLL gene vectors and densely PEGylated gene vectors consisted of spherical and ellipsoidal particles. Un-PEGylated PLL gene vectors had an average major diameter of 82 nm and an average minor diameter of 46 nm. Analysis of PLL-PEG gene vector sizes (Table 3) revealed a major diameter of 177±8 nm and a minor diameter of 16±1 nm. The major diameters of densely PEGylated gene vectors were ~2 fold smaller than PLL-PEG gene vectors, while the minor diameters were ~2 fold larger. PLL-BrPEG gene vectors formed at an N/P ratio of 5 had significantly lower major and minor diameters in comparison to gene vectors formed at an N/P ratio of 2. Gene vector aspect ratios, calculated using the major and minor diameters, were found to be 1-4 fold lower for particles formed incorporating the PLL-BrPEG polymer (FIG. 10, Table 3). The range of aspect ratios was also lower in the case of densely PEGylated particles which was reflected in the lower polydispersity observed for gene vectors incorporating the PLL-BrPEG polymer (FIG. 10, Table 3). Addition of un-PEGylated PLL generated particles with significantly smaller aspect ratios (FIG. 10).

TABLE 3

Physicochemical characterization of gene vectors.

| | Hydrodynamic diameter (nm) ± SEM | Major diameter (nm) ± SEM | Minor diameter (nm) ± SEM | Aspect Ratio ± SEM | Zeta Potential (mV) ± SEM | PDI |
|---|---|---|---|---|---|---|
| PLL-PEG (N/P 2) | 171 ± 5 | 177 ± 8 | 16 ± 1 | 12.0 ± 0.5 | 1.5 ± 0.6 | 0.31 |
| PLL (N/P 2) | 108 ± 13 | 82 ± 6 | 46 ± 3 | 2.4 ± 0.4 | 10.0 ± 1.2 | 0.21 |

TABLE 3-continued

Physicochemical characterization of gene vectors.

|  | Hydrodynamic diameter (nm) ± SEM | Major diameter (nm) ± SEM | Minor diameter (nm) ± SEM | Aspect Ratio ± SEM | Zeta Potential (mV) ± SEM | PDI |
|---|---|---|---|---|---|---|
| BR 50 (N/P 2) | 135 ± 6 | 95 ± 3 | 43 ± 3 | 3.2 ± 0.1 | 1.1 ± 0.7 | 0.26 |
| BR 90 (N/P 2) | 127 ± 3 | 87 ± 6 | 34 ± 2 | 4.0 ± 0.5 | 2.2 ± 1.1 | 0.20 |
| BR 100 (N/P 2) | 142 ± 5 | 117 ± 1 | 32 ± 2 | 6.1 ± 0.4 | 2.2 ± 0.9 | 0.28 |
| BR 50 (N/P 5) | 119 ± 8 | 90 ± 3 | 42 ± 3 | 2.9 ± 0.2 | 2.8 ± 0.2 | 0.24 |
| BR 90 (N/P 5) | 129 ± 6 | 77 ± 2 | 32 ± 2.4 | 3.2 ± 0.1 | 1.4 ± 0.4 | 0.24 |
| BR 100 (N/P 5) | 125 ± 4 | 89 ± 6 | 27 ± 3 | 4.8 ± 0.6 | 2.1 ± 0.4 | 0.24 |

Table 3: Physicochemical characterization of gene vectors. Hydrodynamic diameter (Z average), ζ-potential and polydispersity (PDI) were measured by laser Doppler anemometry and dynamic light scattering in 1/15X PBS at pH 7.0 and are represented as the arithmetic mean of 3 measurements ± standard error (SEM), major and minor diameters were measured from TEM images for at least 100 particles each from 3 particle samples, using ImageJ, and are presented as the arithmetic mean ± SEM.

Figures 11A, 11B, 11C, 11D:
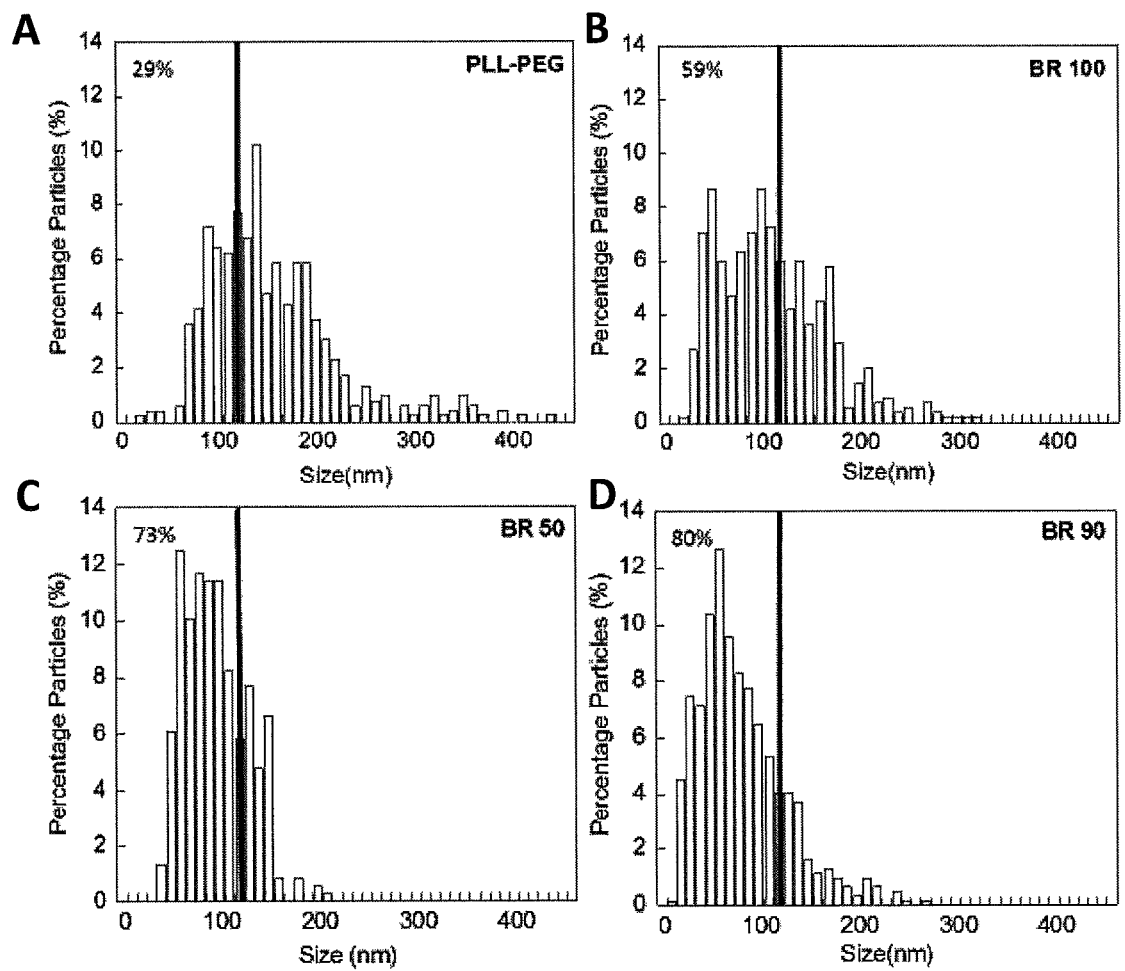
FIGS. 11A to 11D are a histograms showing the percentage of particles (%) over size (nm) of the major diameter of particles consisting of Poly L-lysine and PEG (PLL-PEG) (FIG. 11A), Poly L-lysine and 100% branched PEG (BR 100) (FIG. 11B), Poly L-lysine and 50% branched PEG (BR 50) (FIG. 11C) and Poly L-lysine and 90% branched PEG (BR 90) (FIG. 11D), respectively. The vertical bar represents a cut-off of 114 nm.

Well PEGylated nanoparticles can rapidly diffuse in the brain parenchyma provided their diameter is small enough to allow for movement through the pores in the ECM. In fact, particles with dense PEG coating smaller than 114 nm exhibited rapid diffusion in the ECM [4]. For this reason which particle formulations would have a majority of the population with a size below this cut-off were examined. Only 29% PLL-PEG gene vectors had a major diameter below 114 nm (FIG. 11). To study the effect of using BrPEG in gene vector formulations, the distribution of major diameters of particle populations formulated at an N/P ratio of 2 were compared. Blending of PLL-BrPEG and un-PEGylated PLL polymers at a ratio of 90:10 (BR 90) resulted in a population where ~80% of the particles had a major diameter below 114 nm. This was significantly higher than the percentage of particles below this cut-off for the BR 100 and BR 50-50 formulations, ~59% and ~73% respectively. Although the minor diameters for all the densely PEGylated formulations were larger than the minor diameter of conventional PLL-PEG gene vectors, they were still below the designated cut-off and would therefore not be expected to negatively impact gene vector diffusion.

Given that the particles formulated here are not spherical in nature, the hydrodynamic diameter, defined as the diameter of a sphere that has the equivalent translational diffusion coefficient as the particle, is a useful parameter to describe and compare diffusivity characteristics. The hydrodynamic diameter, measured as the Z average, was found to be lower for all formulations formed using the densely PEGylated polymer (Table 3). The surface charge is also an important aspect affecting diffusion since highly charged particles are more likely to electrostatically interact with the ECM. No significant differences were noted in surface charge between the PEGylated particle formulations. The surface charge of un-PEGylated PLL gene vectors was ~5 fold higher than the PEGylated formulations.

Non-specific interactions of conventional nanoparticles with components of the ECM impede nanoparticle distribution in the brain parenchyma, thus affecting their ability to reach target cells and achieve therapeutic effect. Effectively shielding the nanoparticle surface with a dense layer of PEG minimizes these adhesive interactions and allows for efficient particle penetration through the ECM. In this study, a widely used, clinically tested gene vector was used to achieve widespread and sufficiently high transgene expression in the brain. The complexation parameters were analyzed for the formulation of densely coated gene vectors and thoroughly characterized them to investigate their applicability for subsequent in vitro and ex vivo evaluation.

PEGylation of PLL with a single, linear PEG and multi-arm branched PEG was achieved and verified by NMR. PLL-PEG polymers were found to complex DNA to form conventionally PEGylated gene vectors that satisfactorily mimicked the clinically tested system. Modification of PLL polymers through PEG grafting has previously been reported to form spherical gene vectors with a diameter ~100 nm. The use of the PLL and branched PEG di-block also resulted in the formation of particles with a distinctly different morphology from the conventional PLL-PEG system. However in this case, both spherical and ellipsoid gene vectors with a range of aspect ratios were formed. Despite the steric hindrance imposed by the increased amount of hydrophilic PEG chains that may lead to inferior DNA complexation, gene vector formulated with PLL-BrPEG but with the incorporation of small amounts of un-PEGylated polymer resulted in more uniform nanoparticles with a smaller range of aspect ratios. Moreover, the inclusion of un-PEGylated polymer core lead to the formulation of a large population of nanoparticles with major diameter lower than 114 nm, thereby minimizing the possible steric hindrances that these nanoparticles would encounter in the brain parenchyma. However, the movement of non-spherical particle is influenced by a number of parameters and cannot be easily predicted as particles may align or tumble in the presence of flow and therefore their behavior must be experimentally characterized Example 8: Characterization of Nanoparticles Containing Poly L-Lysine and Branched PEG In Vitro Materials and Methods Cell Culture 9 L rat Gliosarcoma cells were provided by Dr. Henry Brem and were cultured in Dulbecco's modified Eagle's medium (DMEM, Invitrogen Corp., Carlsbad, Calif.) supplemented with 1% penicillin/streptomycin (pen/strep, Invitrogen Corp., Carlsbad, Calif.) and 10% heat inactivated fetal bovine serum (FBS, Invitrogen Corp., Carlsbad, Calif.). Rat brain primary astrocytes were provided by Dr. Arun Venkatesan. Rat brain primary mixed cultures were isolated form neonatal P3-P6 rats and astrocytes were isolated with the conventional shake off method.

Cells were cultured in DMEM/F12 (Invitrogen Corp., Carlsbad, Calif.) supplemented with 10% FBS and 1% penicillin-streptomycin. As per assay requirements, cells were trypsinized by incubating with 0.25% Trypsin EDTA (Corning Inc., Tewksbury, Mass.) for 5 minutes at 37° C. followed by neutralization with media and were seeded in 96-well or 24-well plates and allowed to adhere overnight.

Cell Uptake

For cellular uptake studies, cells were seeded at a density of 50,000 cells per well in 24-well plates, and were treated for 3 hours at 37° C. with 1 µg DNA/well in its compacted nanoparticle form for the different particle formulations. To enable fluorescence sorting by the BD Accuri C6 Flow Cytometer, Cy3 labeled DNA was used for nanoparticle synthesis. The use of labeled DNA did not affect the formation of DNA nanoparticles as confirmed by TEM and ζ-potential. For flow cytometry, the cells were treated briefly with 0.04% trypan blue to quench extracellular florescence, washed in PBS three times and then trypsinized. The trypsin was neutralized and the cells were collected by spinning down at 1000 rcf for 10 minutes. The cell pellet obtained was resuspended in 100 µl of 10% FBS in PBS and kept on ice until the samples were processed. Nanoparticle cell uptake was measured using the Accuri C6 flow cytometer (BD Biosciences, USA) with a 488 nm laser and an FL2 band-pass filter with emission detection wavelength of 585/40 nm. Data were analyzed using the BD Accuri C6 software. Thresholds were determined using untreated samples and gene vector cell uptake was compared to free plasmid.

Luciferase Assay

Cells were seeded at a density of 50,000 cells per well in a 24-well plate and treated with 1 mg/ml compacted pBal DNA in DMEM supplemented with 10% FBS and 1% penicillin-streptomycin for 3 hours at 37° C. Cells were then cultured in fresh media as normal for 3 days before being assayed for luciferase expression. For luciferase extraction the media was removed and the cells were washed twice with 1×PBS. 500 µl of 1× Reporter Lysis Buffer (Promega, Madison, Wis.) was added to each well and incubated for 10 minutes at room temperature. The cells and buffer from each well were transferred to separate microcentrifuge tubes and subjected to three freeze-thaw cycles and then spun down at 1,000 rpm for 5 minutes. The supernatant was transferred into a new microcentrifuge and assayed immediately for luciferase activity. 100 µl of the luciferase substrate-assay buffer mixture (Promega, Madison, Wis.) was added to a polystyrene tube followed by 20 µl of the supernatant and the luminescence was measured immediately using a 20/20n luminometer (Turner Biosystems, Sunnyvale, Calif.). The relative light unit (RLU) was normalized with the total protein concentration measured by Micro-BCA protein assay (Pierce Protein Biology Products, Rockford, Ill.).

Toxicity Assay

In vitro cytotoxicity of gene vectors was measured using the Cell Counting kit-8 supplied by Dojindo Molecular Technologies Inc, Rockville, Md. 10,000 cells/well were seeded in 96-well plates and treated with 1, 5, 10, 50 and 100 µg/ml compacted DNA for 24 hours in DMEM. The media was then replaced with 100 µl DMEM containing 10% FBS and 1% penicillin-streptomycin and 20 µl of Cell Counting kit-8 reagent was added and incubated for 2 hours. Results were measured spectrophotometrically at 450 nm using the Synergy Mx Multi-Mode Microplate Reader (Biotek, Instruments Inc.).

Results

Toxicity

Figure 12:
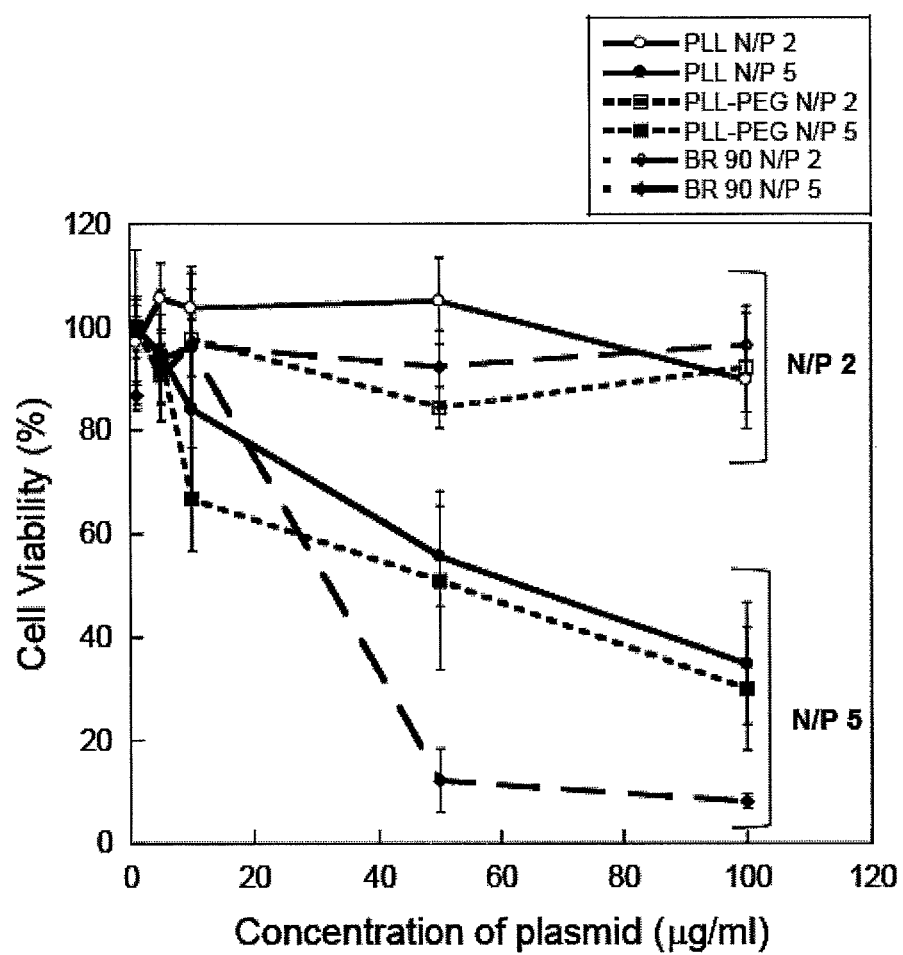
FIG. 12 is a graph showing the % cell viability over concentration of plasmid (µg/ml) for PLL N/P 2 (⊖), PLL N/P 5 (●), PLL-PEG N/P 2 (⊟), PLL-PEG N/P 5 (■), BR 90 N/P 2 (◇) and BR 90 N/P 5 (◆), respectively. Error bars depict SEM.
Figure 13A:
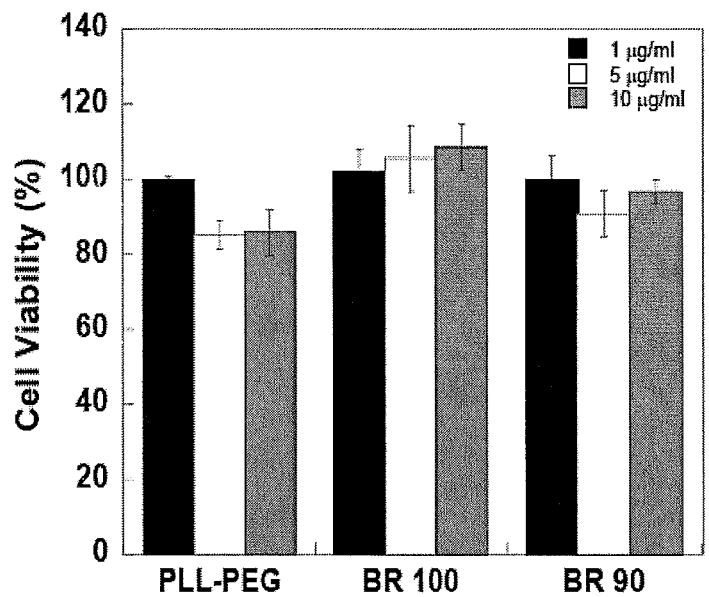
FIGS. 13A and 13B are histograms showing the percentage of cell viability (%) for PLL-PEG, BR 100 and BR 90 at concentrations of 1 µg/ml, 5 µg/ml and 10 µg/ml, for 9 L glioma cells (FIG. 13 A), and primary rat astrocyte cells (FIG. 13 B), respectively. Error bars depict SEM.
Figure 13B:
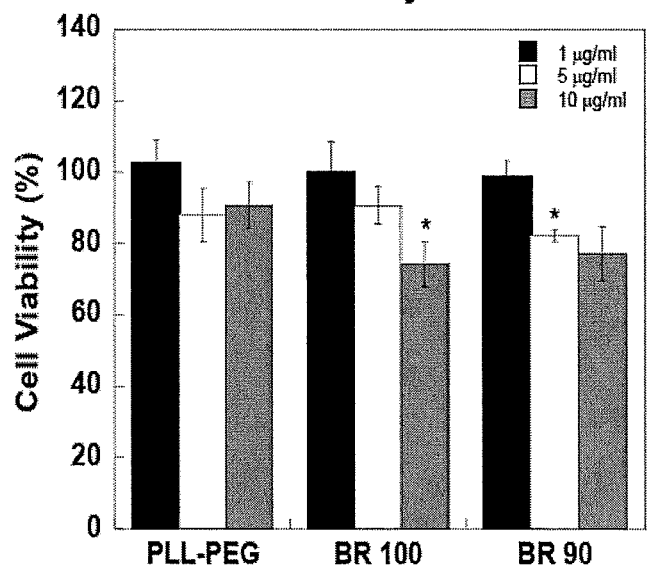

Cell viability assays on 9 L cells revealed increased toxicity of particles formulated at high ratios of polymer to DNA (N/P 5) compared to their low N/P ratio counterparts (FIG. 12). The most toxic formulation was the densely PEGylated gene vector, BR 90, formed at an N/P ratio of 5. However cell viability assays for all particles at an N/P ratio of 2 for 9 L cells (FIG. 12) revealed that gene vectors were relatively non-toxic even at concentrations as high as 100 µg/ml, ~75% viability for all formulations tested. Further cell viability studies revealed that the toxicity of gene vectors formulated at N/P 2 was low at concentrations up to 10 µg/ml for both 9 L cells and rat primary astrocytes (FIGS. 13A and 13B).

Cell Uptake

Figures 14A, 14B:
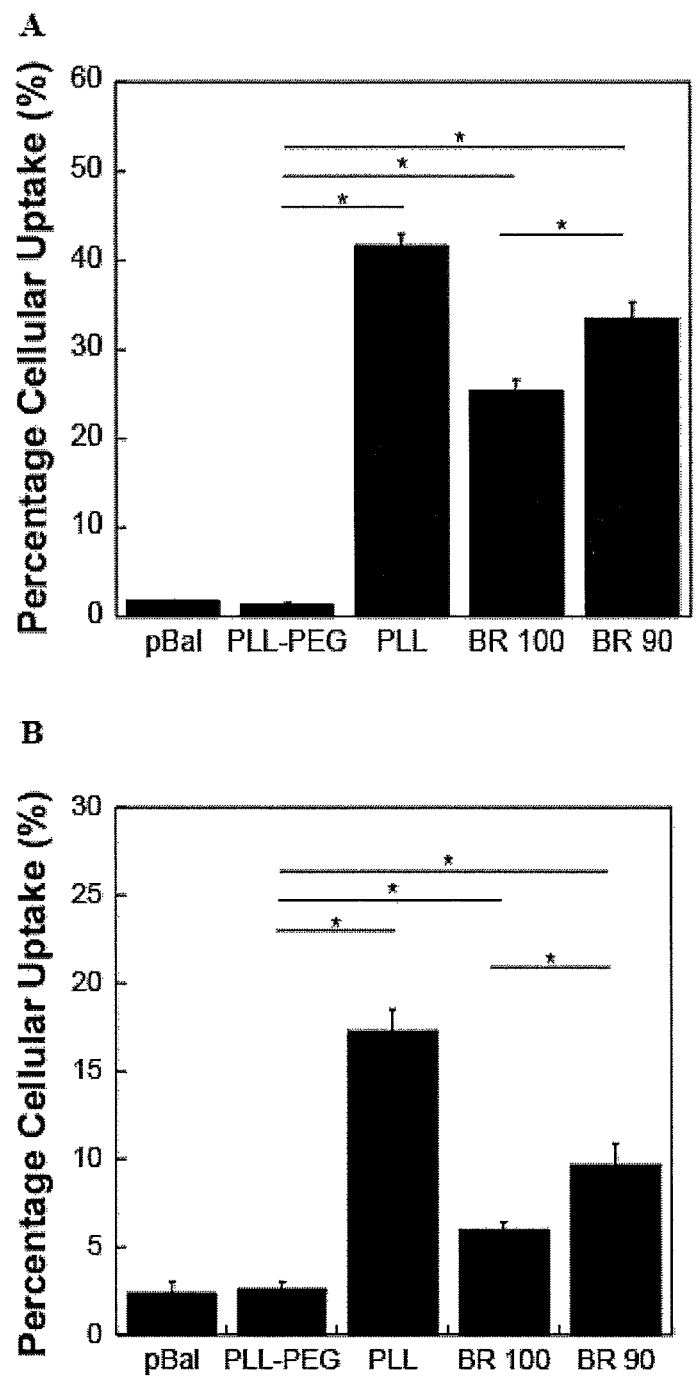
FIGS. 14A to 14D are histograms showing the percentage of cellular uptake (%) for pBal PLL-PEG, PLL BR 100 and BR 90, for 9 L glioma cells (FIG. 14A), and primary rat astrocyte cells (FIG. 14B), and luciferase gene expression (RLU/mg of protein) following in vitro gene vector transfection of 9 L glioma cells (FIG. 14C), and primary rat astrocyte cells (FIG. 14D), respectively. Data represents the mean±SEM. * Denotes statistical significance P<0.05.

Flow cytometric analysis showed increased uptake in the order of PLL>BR 90>BR 100>PLL-PEG for the different formulations (FIGS. 14A and 14B) with differences between particles being significant (p value<0.05). The same trend was observed for 9 L tumor cells and primary rat astrocytes. However absolute values indicated that overall gene vector uptake was higher for 9 L cells. The uptake of PLL-PEG was close to levels observed for free plasmid in both cell lines.

Transfection

Figures 14C, 14D:
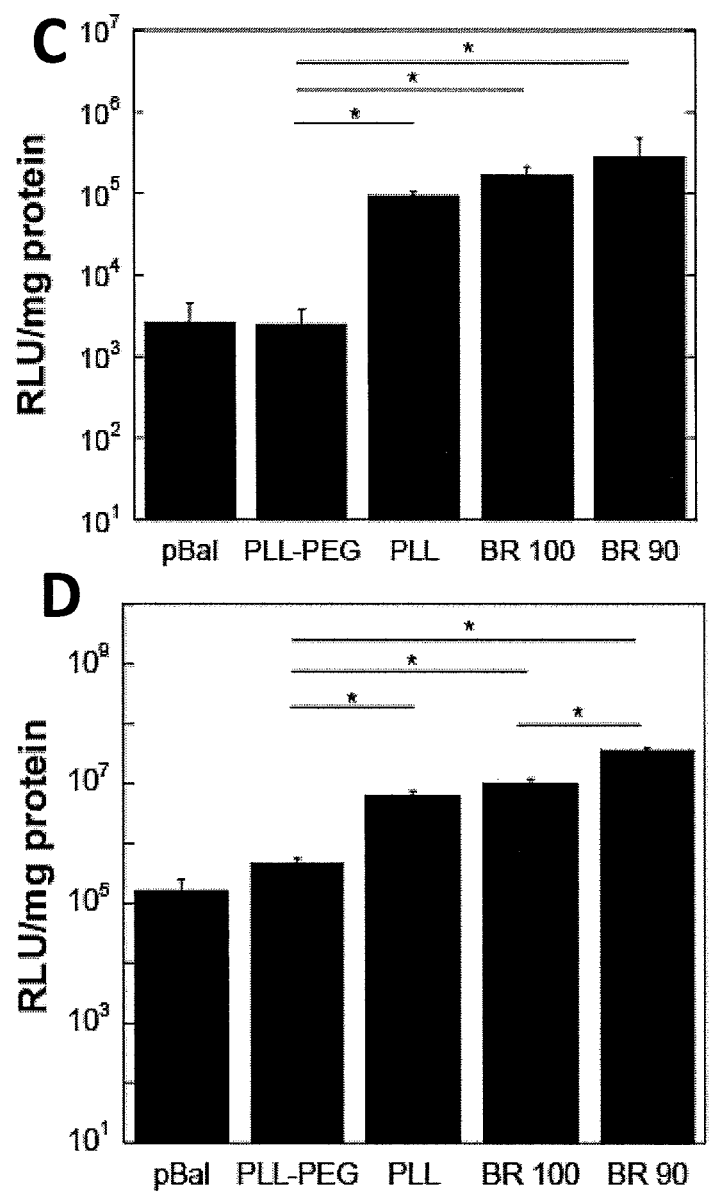

Luciferase activity, measured in Relative Luminescence Units (RLU) (FIGS. 14C and 14D) in both 9 L cells and primary astrocytes was highest for the BR 90, followed by the BR 100, PLL and finally PLL-PEG formulations. Differences were found to be significant only for primary astrocytes where transfection levels for BR 90 were significantly higher than those for all other formulations tested. Transfection of PLL-PEG was comparable to levels achieved by free plasmid.

The toxicity of cationic polymers has been one of the most prominent factors limiting their clinical applicability. It is therefore important to ensure low levels of toxicity for any proposed gene vector platform. The conventional PLL-PEG formulation tested in clinical trials was found to be non-toxic. Low in-vitro toxicity of PLL-PEG at an N/P of 2 verified its applicability as a safely administrable gene vector. PLL-PEG gene vectors were found to be toxic when the N/P ratio was increased to 5 and this result was replicated for the rest of the formulations tested. Previous reports in literature have also indicated an increased toxicity of PLL based gene vectors with increasing N/P ratios. As a result of the high toxicity of gene vectors observed at N/P 5, only the gene vectors formulated at N/P 2 were further characterized. Additional cell viability assays conducted on 9 L and primary cells demonstrated low gene vector toxicity even at the highest treatment concentrations tested and confirmed that gene vectors were not toxic for either cell line at concentrations used for subsequent in-vitro studies.

In-vitro characterization of gene vector internalization revealed that cellular uptake increased as the aspect ratio decreased, with PLL-PEG (average aspect ratio of 12) and PLL (average aspect ratio 2) gene vectors exhibiting the lowest and highest cellular uptake respectively. The observation is in line with previous experimental studies that have shown particles with low aspect ratios to exhibit more rapid cell internalization. Specifically, gold nanospheres with diameters of 14 nm or 74 nm have been shown to be taken up by HeLa cells more than three times as often as 74 14 nm rods (aspect ratio 5). Similarly higher aspect ratios have demonstrated reduced cellular uptake of polymer based gene vectors formed using N-(2-hydroxypropyl) methacrylamide (HMPA)-oligolysine brush polymers. While acknowledging these findings, it is difficult to draw comparisons between such experimental studies due to variations in particle chemistry and cell lines tested. Theoretical models based on energy considerations have also proposed that particles with low aspect ratios are associated with minimum wrapping time, whereas particles lying parallel to the cell are only partially wrapped if too elongated ("frustrated endocytosis"). Although reduced uptake of particles with high aspect ratios has been demonstrated, comparisons between spherical and ellipsoidal nanoparticles have shown that a slightly elongated shape may in fact improve cell uptake. Employing a top-down approach called PRINT, Gratton et al. have demonstrated that internalization of cylindrical particles of cross-linked PEG-based hydrogels with an aspect ratio of three was about four times as fast as their spherical counterparts of the same volume. Similar aspect ratios were observed for the densely PEGylated formulations and conferred a significant advantage in cellular uptake over the conventional PLL-PEG gene vectors for the cell lines studied. The lower aspect ratios achieved while still maintaining non-spherical character appear to be ideal for gene vector internalization.

Despite high cellular uptake, PLL did not exhibit higher transfection efficiencies as compared to BR 100 and BR 90. This may be due to several intracellular factors, including lysosomal degradation, diffusional constraints and metabolic degradation in the cytoplasm. The densely PEGylated BR 90 formulation exhibited the highest transfection efficiency in both 9 L cells and rat primary astrocytes presumably due a combined effect of high cell uptake followed by efficient intracellular trafficking to the nucleus.

Figure 15A:
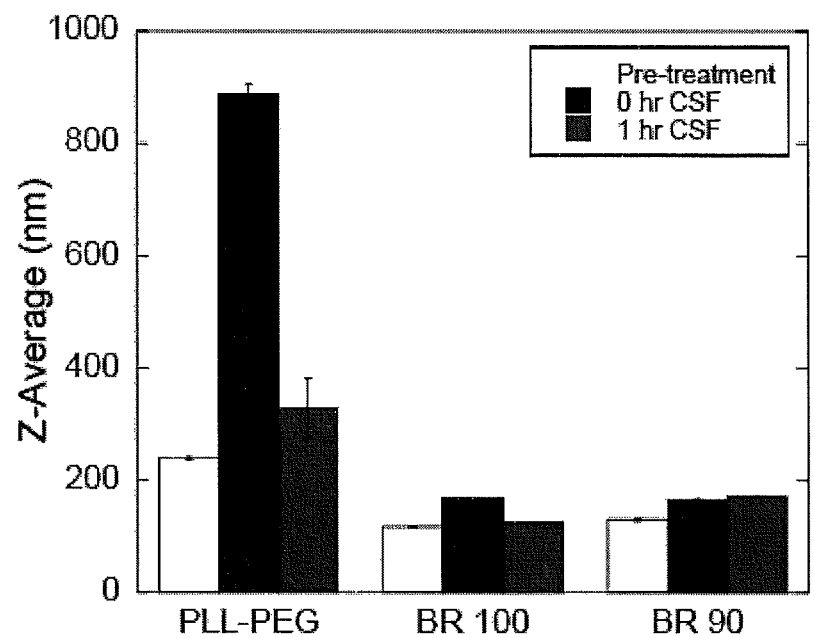
FIGS. 15A and 15B are histograms showing the gene vector Z-average (nm) (FIG. 15A) and polydispersity (PDI) (FIG. 15B), respectively, for PLL-PEG, BR 100 and BR 90 at pretreatment, 0 hour and one hour after treatment with aCSF at 37° C.
Figure 15B:
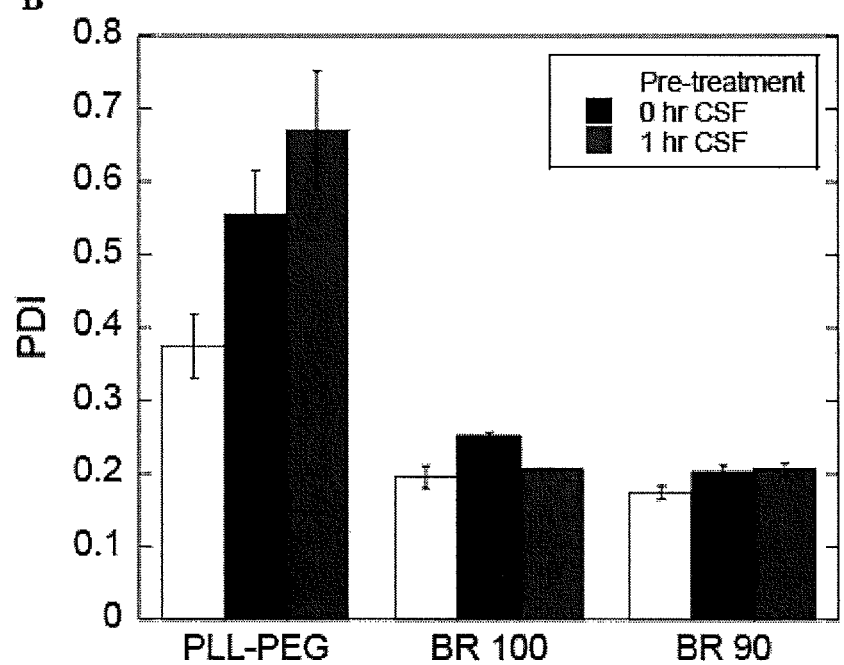
Figure 16:
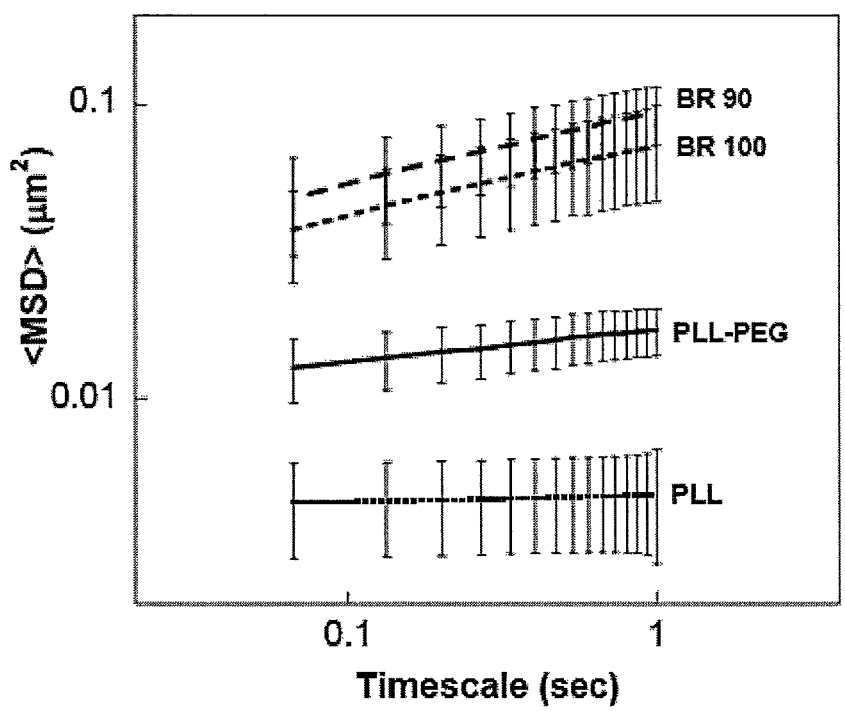
FIG. 16 is a graph showing the ensemble-averaged geometric mean square displacements <MSD> (µm$^2$) over timescale (Sec) for PLL, PLL-PEG, BR 100 and BR 90, respectively. Data represent the ensemble average of at least three independent experiments with N≥500 particles tracked for each experiment, error bars depict SEM.
Figure 17:
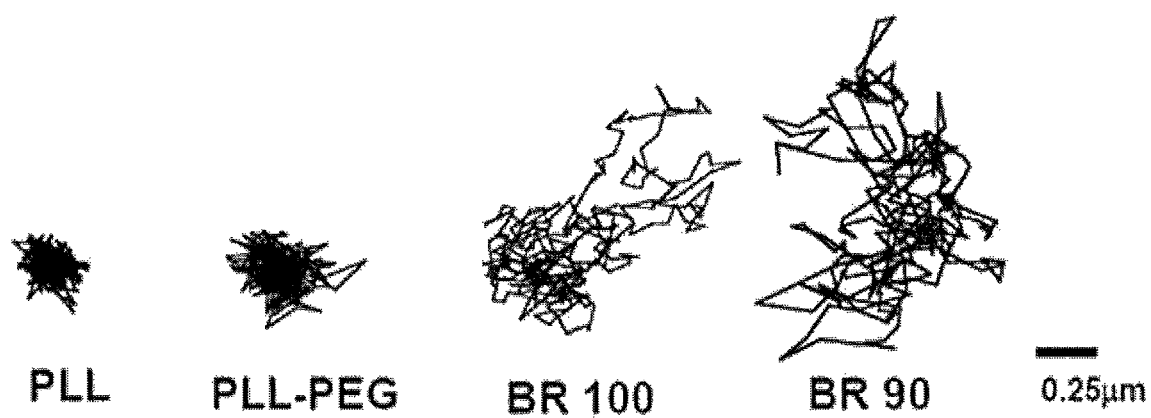
FIG. 17 is a schematic showing the representative particle trajectories over 20 s. Trajectories shown are of particles that had an MSD equal to the ensemble average at a time scale of 1, Scale bar=0.25 µm.
Figure 18:
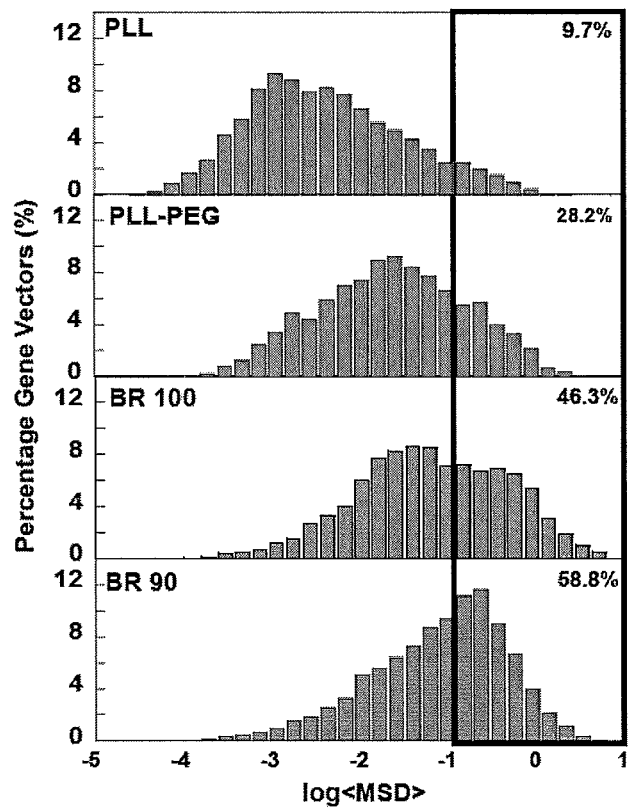
FIG. 18 is a panel of histograms showing Percentage Gene Vector (%) over log <MSD> for gene vectors for PLL, PLL-PEG, BR 100 and BR 90, respectively. Data are taken from at least three independent experiments at a timescale of 1 s.

Example 9: Nanoparticles Containing Poly L-Lysine and Branched PEG have High Diffusivity in Brain Tissue Ex Vivo and In Vivo Materials and Methods
Particle Stability in aCSF Gene vector stability was assessed by incubating in aCSF (Harvard Apparatus, MA) at 37° C. and recording Z-average and polydispersity (PDI) by dynamic light scattering before treatment and 0 hours and 1 hour after treatment using Zetasizer Nano ZS90 (Malvern Instruments, Southborough, Mass.). Measurements were performed at 25° C. at a scattering angle of 90°. TEM girds were also prepared as discussed in section 2.4.2.2 at different time-points including pre-incubation, immediately post-incubation (0 hour), 1 hour post-incubation and 24 hours post incubation.
Preparation of Rodent Brain Slices All animal experiments were carried out at Johns Hopkins University School of Medicine following National Institutes of Health guidelines and local Institutional Animal Care and Use Committee regulations. Briefly, adult Fisher rats (120-140 g) were euthanized with overdose of isoflurane and their brains rapidly removed and immersed in cold aCSF (Harvard Apparatus, MA) supplemented with 10% glucose for 10 minutes. The brain were then sliced to 1.5 mm thick slices using a Zivic brain matrix slicer (Zivic Instruments, Pittsburgh, Pa.) and placed on custom made slides. Half a microliter of fluorescently labeled gene vectors was injected on the cerebral cortex at a depth of 1 mm using a 50 ul Hamilton Neuro Syringe (Hamilton, Reno, Nev.) mounted on a stereotaxic frame. Tissues were covered by a 22 mm×22 mm coverslip to reduce tissue movement and bulk flow.
Multiple Particle Tracking Particle trajectories were recorded over 20 seconds at an exposure time of 66.7 ms by a Evolve 512 EMCCD camera (Photometrics, Tucson, Ariz.) mounted on an inverted epifluorescence microscope (Axio Observer D1, Zeiss; Thornwood, N.Y.) equipped with a 100×/1.46 NA oil-immersion objective. Movies were analyzed by extracting x, y-coordinates of gene vectors centroids over time and the mean square displacement of each particle was calculated as a function of time. At least N=3 rat brains were used per gene vector type and at least 500 gene vectors were tracked per sample. The geometric mean of the MSDs for all nanoparticles was calculated per sample and the average of different rodent brains was calculated as a function of time. Histograms were generated from the MSD of every nanoparticle at a time scale of $\tau$=1 sec
In Vivo Co-Injection To study nanoparticle diffusion in vivo, equal concentrations of differentially fluorescently labeled PLL-PEG and BR 90 nanoparticles were co-injected into the striatum of female Fischer 344 rats (n=3). The rodents were anesthetized with a mixture of ketamine-xylazine and a mid-sagittal incision was made to expose the bregma. The striatum was targeted 0.5 mm posterior to the bregma and 3 mm lateral to the midline. The nanoparticle loaded 50 µl Hamilton Neuros syringe was lowered 3.5 mm below the dura. Gene vectors at individual concentrations of 0.25 µg/µl were administered at a rate of 0.33 µl/min, using a Chemyx Inc. Nanojet Stereotaxic syringe pump (Chemyx, Stafford, Tex.), for a total of 20 µl followed by withdrawal of the syringe. The animal was sutured and placed on a heating pad before returning to its cage. After 2 hours the rodent was sacrificed, the brain was removed, and fixed in formalin overnight. The suspension solution was then changed to 15% sucrose and subsequently to 30% sucrose after 24 hours. The brain was sliced using a Leica CM 1905 cryostat to obtain slices of 100 µm thickness. The slices were stained with DAPI (Molecular Probes, Eugene, Oreg.) and imaged using the Zeiss LSM 510 Meta Confocal Microscope at 5× magnification (Carl Zeiss; Hertfordshire, UK). Microscope settings were kept constant during imaging. Brain slice images were quantified for fluorescent distribution of BR 90 or PLL-PEG nanoparticles by running the confocal laser scanning microscope images through a custom MATLAB script which thresholded the images at 10% of the maximum intensity. Care was taken to avoid quantifying fluorescent distribution in the ventricles or white matter tracts. The area of distribution calculated from each slice was multiplied by the slice thickness of 100 µm and summated across all images to obtain a total volume of distribution.
Results
Particle Stability in aCSF Gene vector stability was investigated in aCSF to model the physicochemical characteristics of the gene vectors following injection into the brain. The PLL-PEG formulation was unstable immediately upon immersion in CSF as both Z-average and the polydispersity index (PDI) increased significantly when compared to particle characteristics measured prior to treatment (FIG. 15). At one hour after treatment, the PDI further increased while a drop in the Z average was registered. For both the highly PEGylated formulations, BR 100 and BR 90, a slight increase in Z-average and PDI was observed immediately after CSF treatment. In the case of BR 100, both measured values dropped at the one hour time-point where as the Z-average and PDI maintained at the same levels for BR 90. These results were corroborated with TEM images taken for each sample at the same time-points.
Particle Diffusion Automated tracking of gene vectors was used to obtain the ensemble geometric mean square displacement up to a timescale of τ=1 second for each tissue sample and was then averaged over three different samples. The densely PEGylated gene vectors showed improved transport over the conventional PLL-PEG (FIG. 16). The MSDs at τ=1 second for BR 90 and BR 100 were 5.6 and 4.2 fold higher than that of the conventional PLL-PEG formulation. The differences between BR 90 and BR 100 were not found to be significant. The increased log(MSD) for the densely PEGylated nanoparticles can also be seen in the histogram plots (FIG. 18). When analyzing individual gene vector MSDs, a greater percentage of particles with log 10MSD≥−1, defined as rapidly moving, were observed for BR 90 (58.8%) and BR 100 (46.3%) versus PLL-PEG (28.2%). Representative particle trajectories (FIG. 17) depict the poor diffusivity of PLL-PEG while BR 90 and BR 100 were diffusive over large distances. PLL particles were completely immobilized.

In Vivo Co-Injections

Figure 19:
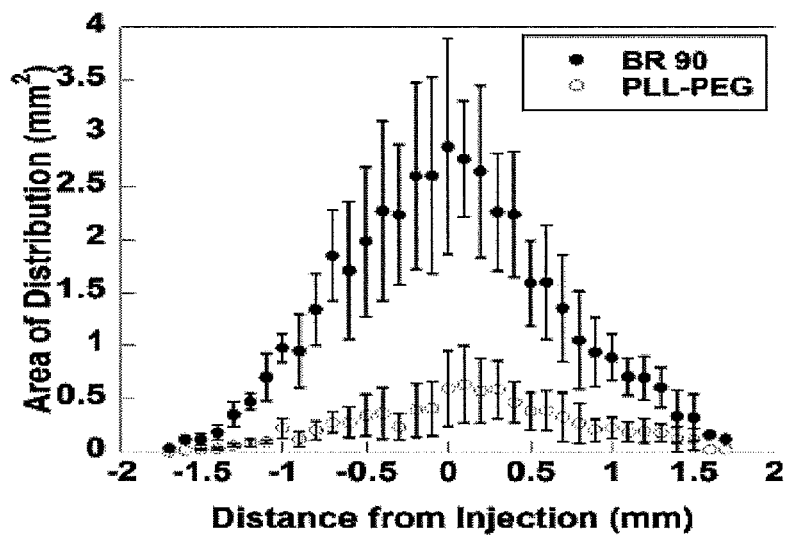
FIG. 19 is a graph showing area of distribution (mm$^2$) of gene vectors as a function of distance from injection site (mm) for BR90 (●) and PLL-PEG (○) respectively, quantified from individual confocal images of 100 µm slices of brain tissue. N=3, error bars represent standard error in mean.
Figure 20:
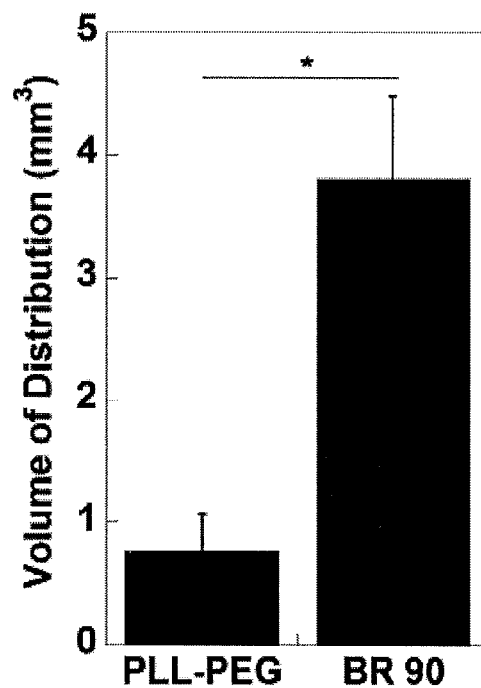
FIG. 20 is a histogram showing volume of distribution of gene vectors (mm$^3$) for BR90 and PLL-PEG, respectively, quantified from confocal images of 100 µm slices of brain tissue. * Denotes statistical significance, P value<0.05.

In vivo co-injections of gene vectors revealed that densely PEGylated BR 90 particles were able to distribute further than the conventionally PEGylated PLL particles. Quantitative analysis of confocal images showed that the areas of distribution followed a bell shaped curve (FIG. 19), with maximum distribution in the plane of the site of injection. The volume of distribution for the densely PEGylated gene vector was approximately four fold higher than that for PLL-PEG (FIG. 20).

Figure 22A:
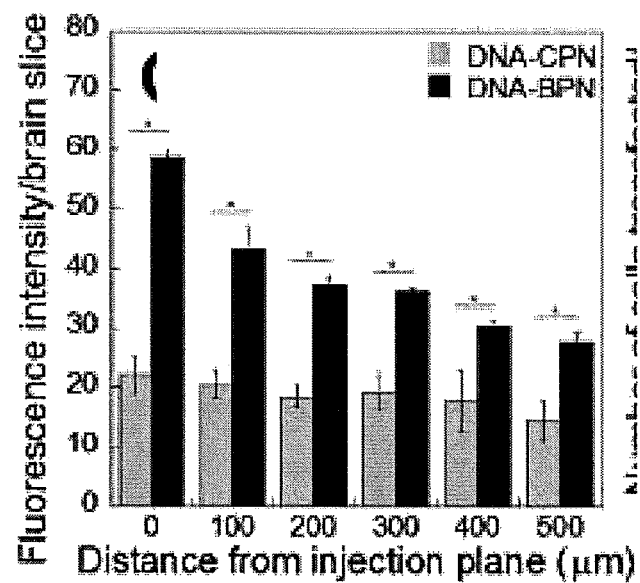
FIG. 22A is a bar graph showing fluorescence intensity per brain slice at different distances (µm) from injection plane following injection of BR90 (DNA-BNP) or PLL-PEG (DNA-CNP).
Figure 22B:
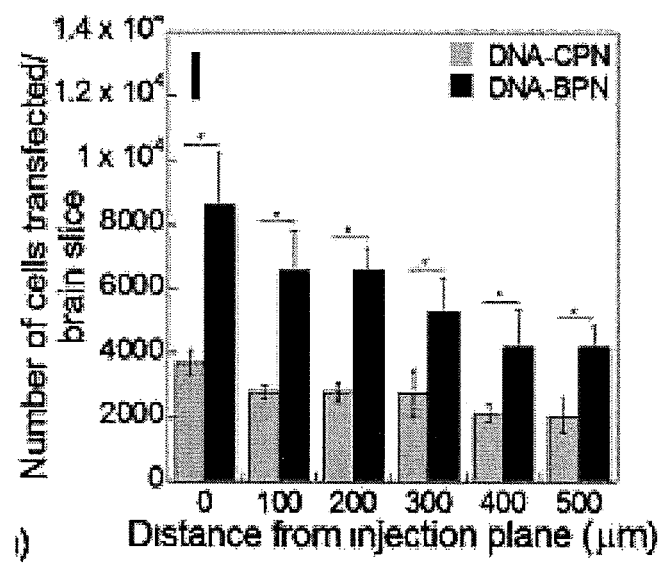
FIG. 22B is a bar graph showing the number of cells transfected per brain slice at different distances (µm) from injection plane following injection of BR90 (DNA-BNP) or PLL-PEG (DNA-CNP). * Denotes statistical significance p<0.05.

The concurrent improvement in brain penetration and in vitro transfection efficiency achieved with DNA-BPN in comparison to DNA-CPN led to enhanced and more widespread transgene expression in vivo, as demonstrated with CED. Quantitative analysis of the integrated density (FIG. 22A) and number of cells transfected per brain slice at distances up to 500 µm away from the injection plane, revealed a significant, approximately 2-3 fold increase, for BR 90 (N/P2) particles (DNA-BPN) in comparison to PLL-PEG particles (DNA-CPN) (FIG. 22B).

PLL-PEG exhibited limited diffusion in the brain parenchyma. In contrast, densely PEGylated PLL gene vectors exhibit significantly improved diffusivities in ex vivo and in vivo rodent brain tissue as compared to the conventional PLL-PEG system. Among the densely PEGylated formulations, the marginally higher diffusivity of BR 90 compared to BR 100, could potentially be reflecting subtle differences in physicochemical characteristics. For densely PEGylated nanoparticles adhesive interactions with the ECM are drastically minimized and therefore steric hindrances may play a major role. Densely PEGylated particles up to 114 nm are capable of brain penetration while particles of 200 nm are not. Thus, 114 nm is a size cut-off under which densely PEGylated particles can be expected to rapidly diffuse. The incorporation of un-PEGylated polymer to the BR 100 gene vectors resulted in a greater percentage of the population with a major diameter i.e. the larger dimension for non-spherical particles, below 114 nm. This, along with a lower PDI, may have contributed to a larger diffusive fraction of the BR 90 formulation. The increased brain penetrating ability of densely PEGylated PLL gene vectors is a significant improvement over the current widely used PLL-PEG gene vector. In comparison, the particle formulation demonstrates higher stability, in vitro transfection efficiency and diffusivity in the brain ECM, establishing it as a promising platform for gene delivery to the brain.

The PLL based gene vector formulated using a PLL-branched PEG co-polymer and a small amount of un-PEGylated PLL polymer demonstrated both improved diffusion and transfection in comparison to the conventionally used PLL-PEG. Through dense PEGylation, charge based interactions that limit gene vector distribution in the brain parenchyma were minimized, while simultaneously achieving small nanoparticle sizes to minimize steric hindrances and enhancing the volume of distribution through CED. In addition to maximizing therapeutic distribution, the physicochemical characteristics of the densely PEGylated gene vector system also favored improved in vitro cell uptake and transfection. Moreover, the PLL-PEG system has demonstrated a favorable safety profile in clinical trials for treatment of CF, thereby setting an excellent precedence for also translating a densely PEGylated PLL based gene vector system. The combination of rapid diffusion and efficient transgene delivery with a pressure driven administration method opens a window of opportunity for effective non-viral gene therapy of GB.

We claim:

1. A method for delivering an effective amount of therapeutic, prophylactic or diagnostic nucleic acids through the blood brain barrier and through the anisotropic and electrostatically charged extracellular matrix of the brain of a subject, comprising administering to the subject a formulation comprising nanoparticles formed of
   a cationic first polymer; and
   a hydrophilic second polymer selected from the group consisting of a polyethylene glycol and copolymers thereof,
      wherein at least 50% up to 90% of the cationic first polymer is conjugated to the hydrophilic second polymer,
      wherein the first cationic polymer, the hydrophilic second polymer, or both, are branched; and
   the nucleic acids, wherein the nucleic acids are encapsulated within the nanoparticles or associated with the surface of the nanoparticles, and
   wherein the nanoparticles have a diameter of between about 40 nm and about 150 nm and are coated with the hydrophilic second polymer at a density that imparts a near neutral charge and enhances diffusivity through the blood brain barrier and through the anisotropic and electrostatically charged extracellular matrix of the brain.

2. The method of claim 1, wherein the formulation is administered directly to the brain.

3. The method of claim 1, wherein the formulation is administered systemically.

4. The method of claim 1, wherein the formulation is administered in combination with one or more techniques to facilitate passage of the nanoparticles through the blood brain barrier.

5. The method of claim 4, wherein the technique is selected from the group consisting of convection enhanced delivery, electron paramagnetic resonance, ultrasound sonication with or without microbubbles, and use of osmotic agents.

6. The method of claim 1, wherein the subject has one or more symptoms of a disease or disorder selected from the group consisting of tumors, neurological disorders, and brain injury or trauma.

7. The method of claim 1, wherein more than 32.9% of the nanoparticles have an ensemble geometric mean square displacement of at least 0.1 µm$^2$ at a timescale of 1 second in the brain.

8. The method of claim 1, wherein the nanoparticles have a diameter of less than or equal to 114 nm, 100 nm, or 50 nm.

9. The method of claim 1, wherein the hydrophilic second polymer is polyethylene glycol having a molecular weight between 1,000 Daltons and 10,000 Daltons.

10. The method of claim 9, wherein the polyethylene glycol has a molecular weight of 5,000 Daltons.

11. The method of claim 1, wherein the cationic first polymer is branched polyethyleneimine with a molecular weight between 10,000 Daltons and 50,000 Daltons.

12. The method of claim 1, wherein the molar ratio of the hydrophilic second polymer to the cationic first polymer is greater than 8.

13. The method of claim 1, wherein the nitrogen-to-phosphorus ratio of the cationic first polymer and the hydrophilic second polymer to the nucleic acids is at least 2.

14. The method of claim 1, wherein the cationic first polymer is poly-L-lysine.

15. The method of claim 14, wherein the hydrophilic second polymer is branched polyethylene glycol.

16. The method of claim 15, wherein at least 50% of the poly-L-lysine is conjugated with the branched polyethylene glycol.

17. The method of claim 1, wherein the mass of the hydrophilic second polymer is at least 1/10,000, 1/7500, 1/5000, 1/4000, 1/3400, 1/2500, 1/2000, 1/1500, 1/1000, 1/500, 1/250, 1/200, 1/150, 1/100, 1/75, 1/50, 1/25, 1/20, 1/5, 1/2, or 9/10 of the mass of the nanoparticles.

18. The method of claim 1, wherein the weight percent of the hydrophilic second polymer relative to total nanoparticle is at least 80%, 81%, 82%, 83%, 84%, 85%, 86%, 87%, 88%, 89%, 90%, 91%, 92%, 93%, 94%, 95%, or greater.

19. The method of claim 1, wherein the formulation further comprises a pharmaceutically acceptable excipient.

20. The method of claim 5, wherein the osmotic agents comprise mannitol.

* * * * *